(12) United States Patent
Fantuzzi et al.

(10) Patent No.: US 11,179,556 B2
(45) Date of Patent: Nov. 23, 2021

(54) VASCULAR ACCESS

(71) Applicant: ABIOMED EUROPE GMBH, Aachen (DE)

(72) Inventors: Glen Fantuzzi, Arlington, MA (US);
Dion Mraz, Arlington, MA (US);
Daniel A. Raess, Boxford, MA (US);
David A. Brousseau, Raymond, NH (US); Susanna Mayo, Boston, MA (US)

(73) Assignee: ABIOMED EUROPE GMBH, Aachen (DE)

( * ) Notice: Subject to any disclaimer, the term of this patent is extended or adjusted under 35 U.S.C. 154(b) by 413 days.

(21) Appl. No.: 15/517,937

(22) PCT Filed: Oct. 2, 2015

(86) PCT No.: PCT/EP2015/072792
§ 371 (c)(1),
(2) Date: Apr. 7, 2017

(87) PCT Pub. No.: WO2016/055368
PCT Pub. Date: Apr. 14, 2016

(65) Prior Publication Data
US 2017/0312492 A1     Nov. 2, 2017

(30) Foreign Application Priority Data

Oct. 7, 2014  (EP) .................................. 14187972

(51) Int. Cl.
*A61M 39/06*       (2006.01)
(52) U.S. Cl.
CPC . *A61M 39/0613* (2013.01); *A61M 2039/0633* (2013.01); *A61M 2039/0653* (2013.01);
(Continued)

(58) Field of Classification Search
CPC ...... A61M 39/0613; A61M 2039/0633; A61M 2039/0686; A61M 2039/0653;
(Continued)

(56) References Cited

U.S. PATENT DOCUMENTS

| | | | | |
|---|---|---|---|---|
| 4,430,081 A | * | 2/1984 | Timmermans | .... A61M 39/0606 251/149.1 |
| 4,610,665 A | * | 9/1986 | Matsumoto | ....... A61M 39/0606 604/167.04 |

(Continued)

FOREIGN PATENT DOCUMENTS

| | | |
|---|---|---|
| CN | 103813817 A | 5/2014 |
| JP | H11-004894 A | 1/1999 |

(Continued)

OTHER PUBLICATIONS

PCT International Search Report for PCT/EP2015/072792, dated Dec. 17, 2015 (3 pages).

(Continued)

*Primary Examiner* — Katherine M Rodjom
(74) *Attorney, Agent, or Firm* — Botos Churchill IP Law LLP

(57) ABSTRACT

A system for providing vascular access in a patient's body may comprise at least one hemostatic valve (610) and at least one clamp (210) to be used with a vascular graft (110). The vascular graft (110) comprises a tubular body having a proximal end (110A) and a distal end (110B), the proximal end (110A) being configured to be attached to a vessel in a patient's body. The at least one valve (610) is configured to be attached to the distal end (110B) of the graft's tubular body and comprises a housing (616) including a flexible membrane (611) that allows a medical device (810) to be inserted through the membrane (611) into said vascular graft (110). The valve (610) further comprises an introducer sheath (615) configured to be inserted into the distal end (Continued)

(110B) of the graft's tubular body. The at least one clamp (210) is configured to be disposed around the graft's tubular body and has a first configuration that allows insertion of the valve's introducer sheath (615) into the distal end (110B) of the graft's tubular body and a second configuration that allows clamping of the graft (110) against the valve's introducer sheath (615), when inserted in the graft's tubular body.

23 Claims, 22 Drawing Sheets

(52) U.S. Cl.
CPC ............... *A61M 2039/0673* (2013.01); *A61M 2039/0686* (2013.01)

(58) Field of Classification Search
CPC ...... A61M 2039/0673; A61M 39/1011; A61M 39/12; A61F 2/2412; A61F 2/2476; A61F 2/2463
See application file for complete search history.

(56) References Cited

U.S. PATENT DOCUMENTS

| | | | | |
|---|---|---|---|---|
| 5,395,349 A | * | 3/1995 | Quiachon | A61B 17/3462 251/4 |
| 2005/0096605 A1 | * | 5/2005 | Green | A61M 39/06 604/246 |
| 2006/0085060 A1 | * | 4/2006 | Campbell | A61F 2/06 623/1.26 |
| 2008/0097386 A1 | | 4/2008 | Osypka | |
| 2008/0221469 A1 | * | 9/2008 | Shevchuk | A61M 16/0816 600/532 |
| 2009/0018508 A1 | * | 1/2009 | Fisher | A61M 25/0097 604/167.04 |
| 2012/0109063 A1 | | 5/2012 | Hansen | |
| 2012/0310167 A1 | | 12/2012 | Kraus | |
| 2013/0060268 A1 | * | 3/2013 | Herrig | A61M 39/12 606/153 |

FOREIGN PATENT DOCUMENTS

| | | |
|---|---|---|
| JP | 2001149487 A | 6/2001 |
| JP | 2005534370 A | 11/2005 |
| KR | 20140062111 A | 5/2014 |
| WO | WO 2004/010853 | 2/2004 |

OTHER PUBLICATIONS

First Office Action issued in corresponding Korean Patent Application No. 10-2017-7012329 dated May 15, 2020.

* cited by examiner

VASCULAR ACCESS

CROSS-REFERENCE TO RELATED APPLICATIONS

This application is a United States National Stage filing under 35 U.S.C. § 371 of International Application No. PCT/EP2015/075792, filed Oct. 2, 2015, which claims the benefit of European Patent Application No. 14187372, filed Oct. 7, 2014, the contents of all of which are incorporated by reference herein in their entirety. International Application No. PCT/EP2015/075792 published under PCT Article 21(2) in English.

BACKGROUND

Long term vascular access is a common medical procedure used in several medical situations including dialysis for patients requiring frequent dialysis treatments, chemotherapy treatment or ventricular assist device use. Different devices and different methods are used depending on patient needs. Long term vascular access in patients needing ventricular assist devices is common through an open chest procedure and direct cardiovascular access.

Lately there has been a move toward the use of peripheral vessels to access the cardiovascular system in order to avoid traumatic open chest surgery. The move toward the use of peripheral vessels instead of central cardiovascular vessels has been accompanied by the development of a large number of specific devices and tools that are specifically designed for peripheral use. Vascular introducers are the most common devices that have been developed to allow peripheral vascular access. For providing access to a vessel, an introducer usually has a tapered tip and is directly pierced into a vessel, in particular with the help of a dilator. These introducers have been limited to small diameters ranging from 1 to 3 mm and used for a maximum of several hours. Introducers that are used for more than 24 hours face the problem of blood reaction to foreign material residing in the blood stream for long duration.

When it comes to the field of long term larger diameter vascular access, many of the devices and tools used for accessing large diameter vessels of the cardiovascular system in open heart surgery are the same as are used in peripheral vascular access. The use of inappropriate devices, tools and procedures in peripheral vascular access has compromised the potential of peripheral vascular access and resulted in less than optimal results.

Dacron grafts are commonly used in long term vascular access. The same Dacron grafts are commonly used in peripheral access that require large diameter access and are intended to be left in the patient for longer than a few days. These grafts are basically sutured to the vessel at one end, the other end being closed using different methods to guarantee hemostasis. Once blood enters the graft, the porous Dacron mesh is penetrated and clogged by the blood. It is common to use a regular medical silicone plug that is secured with common medical suture to assure hemostasis. However, grafts made from other materials, such as silicone, may also be used. Device introduction into these grafts requires physicians to innovate and experiment with different techniques and tools, leading to unpredictable results and high complication rates. Considering that these procedures involve one of the main vascular vessels, bleeding is the main concern. Therefore, hemostasis is a critical aspect of these procedures. Any failure in hemostasis at any time, during or after device insertion, could lead to significant blood loss or even patient death.

SUMMARY OF THE INVENTION

It is an objective of the present invention to provide devices for achieving access to large vessels or cavities, wherein the access allows the introduction and/or removal of large diameter devices, tissue or fluid through the access in a safe and controlled manner and by a simple procedure.

It is another objective of the present invention to provide a vascular graft that is easily secured to a vessel or cavity, provides hemostasis and allows the introduction or removal of large devices or material.

It is another objective of the present invention to provide a vascular graft equipped at its distal end with a hemostatic valve that allows the introduction or removal of large devices or material.

It is another objective of the present invention to provide a separate hemostatic valve that is designed to be integrated into a graft to provide quick and effective hemostasis during and after a medical procedure requiring access to a vessel or a cavity in the body.

It is another objective of the present invention to provide a device that interfaces with a vascular graft to provide hemostasis during device or material introduction into or removal from the body and to leave in the graft a plug that will provide long term hemostasis and a bacterial barrier during and after the completion of the medical procedure.

It is another objective of the present invention to provide a device that interfaces with an implanted vascular graft that will provide hemostasis and means to easily handle and secure the graft during device or material introduction into or removal from the body and after the completion of the medical procedure.

It is another objective of the present invention to provide methods for using a commonly available or specialized vascular introducer to easily interface with standard vascular grafts to provide hemostasis and a bacterial barrier during or after a medical procedure involving the use of vascular or medical grafts.

It is another objective of the present invention to provide devices that allow the quick and safe introduction or removal of devices or material into or out of a vessel or body cavity that range in diameter from 1 mm to 12 mm.

It is another objective of the present invention to provide a successive introducer sheath equipped with separate hemostasis valves of the same size or range in sizes, which may be used in succession and/or in combination with the integrated hemostasis valve integrated into the graft.

It is another objective of the present invention to provide a successive introducer sheath equipped with separate hemostasis valves of the same size or range in sizes, which may be used in succession and/or in combination with the separate hemostasis valve integrated into the graft.

It is another objective of the present invention to provide a "quick connect" connector adapted to connect quickly to the graft and/or the hemostatic valve.

It is another objective of the present invention to provide a "quick connect" connector adapted to connect quickly to the graft and to any catheter or device passing through the graft.

It is another objective of the present invention to provide a clamp that clamps the hemostasis valve to the graft and any device passing through the graft.

It is another objective of the present invention to provide a detachable hemostasis valve to allow the proper sizing of the graft length.

The invention is described in the accompanying independent claims, wherein preferred embodiments are specified in the dependent claims.

According to one embodiment of the invention, a system for providing vascular access in a patient's body is provided. The system comprises a vascular graft comprising a tubular body having a proximal end and a distal end, the proximal end being configured to be attached to a vessel in a patient's body. The system further comprises at least one valve configured to be attached to the distal end of the graft's tubular body, the valve comprising a housing, the housing including a flexible membrane having at least one of a passage extending through the membrane and a weakened area to allow a medical device to be inserted through the membrane into said vascular graft. The valve further comprises an introducer sheath that is configured to be inserted into the distal end of the graft's tubular body.

It is to be understood that the term "proximal" refers to directions towards the heart, while the term "distal" refers to directions away from the heart. The valve will hereinafter also be referred to as "hemostatic valve", emphasizing its function to provide hemostasis, in other words to seal the distal end of the vascular graft to prevent blood from flowing through the valve during insertion of a medical device, such as a catheter. The present invention provides a hemostatic valve having an introducer sheath that is particularly adapted for insertion into a vascular graft. In other words, in contrast to common introducers, the introducer sheath of the hemostatic valve according to the present invention is not configured for direct insertion into a vessel but is introduced into a vascular graft. The valve that is introduced into the distal end of the vascular graft provides more efficient hemostasis than common techniques like simply clamping the graft or tightening the graft by means of a suture. The membrane may be constructed as a flexible disk or in other configuration providing the function of a check valve, such as a flutter valve.

The system preferably further comprises at least one clamp configured to be disposed around the graft's tubular body and having a first configuration that allows insertion of the valve's introducer sheath into the distal end of the graft's tubular body and a second configuration that allows clamping of the graft against the valve's introducer sheath, when inserted in the graft's tubular body. The clamp provides an easy way to secure the valve in the vascular graft and may also be used for compressing the membrane of the valve.

According to another embodiment of the invention a valve is provided, which is configured for use in such system. The valve comprises a housing including a flexible membrane having at least one of a passage extending through the membrane and a weakened area to allow a medical device to be inserted through the membrane. The valve further comprises an introducer sheath configured to be inserted into an open end of a mating device, the mating device preferably being a vascular graft. The valve may also be integrally formed with a vascular graft. As described above, the introducer sheath is preferably particularly adapted for insertion into a vascular graft. It is not configured for direct insertion into a vessel.

Preferably an outer surface of the introducer sheath includes at least one retention structure so as to restrain removal of the valve from said mating device into which it is inserted. The retention structure may be formed as a ramped surface, preferably comprising at least one barb that tapers away from the outer surface of the introducer sheath in a direction towards the housing. The surface including a retention structure is particularly useful when using the valve with a vascular graft to improve fixation of the valve in the vascular graft. In case the retention structure comprises one or more barbs, the barbs preferably are disposed on the outer surface of the introducer sheath such that a clamp may be positioned distally of the barbs when clamping the valve to a vascular graft. In contrast, common introducers for direct insertion into a vessel have a smooth surface without a retention structure, which would harm the vessel.

It is preferred that, in addition to the membrane, at least a portion of the housing is made of a flexible material, wherein preferably the flexible material is an elastic material. The flexible material may be soft rubber or other soft plastics material, such as silicone, polyurethane or polyvinyl chloride. The introducer sheath may be stiffer with respect to radial compression forces than a portion of the housing where the membrane is positioned. This allows compressing and sealing of the membrane against an inserted medical device by compressing a clamp around the housing of the valve in the area where the membrane is located. The introducer sheath and possibly the distal end of the valve's housing are stiffer to provide stability of the valve.

Preferably, the housing is cylindrical. Providing a cylindrical instead of e.g. a conical shape creates a low profile valve that may be implanted into a patient's body for long term use, e.g. several months. The cylindrical low profile valve allows a clamp to be placed around the valve to tighten the membrane against an inserted medical device, such as a catheter, to prevent blood flow and to secure the device and prevent it from moving longitudinally. An inner diameter of the introducer sheath preferably does not decrease at the introducer sheath's proximal end and may be constant along the entire length of the introducer sheath. For instance, the diameter may range from 5 to 10 mm. In contrast, common introducers taper down at the tip to facilitate insertion into a vessel by means of a dilator.

In a preferred embodiment, the at least one passage extends at least along a portion of the diameter of the membrane, preferably along the entire diameter. The at least one passage in the membrane may comprise at least two slits extending diametrically through the membrane and crossing each other. In addition or alternatively, the membrane may have a hole extending through the membrane, preferably a central hole that may be connected to the slits. The diameter of the hole may be adapted to the diameter of the medical device to be inserted, such as a catheter. In order to facilitate insertion of larger parts, e.g. a catheter pump at the tip of a catheter, slits may be provided to temporarily increase the opening in the membrane during insertion. However, the slits may be omitted, for instance when the hemostatic valve is already pre-mounted on a catheter and is intended to be implanted for a long time. In this case, the slits are not necessary and could present a risk of blood leakage.

The valve may include at least one seam, preferably two diametrically opposing seams, extending along the length of the valve and forming a predetermined breaking line to allow breaking of the valve into two halves along the length of the valve. This allows easy removal ("peel away") of the valve when a medical device, such as a catheter, is inserted through the valve.

In order to facilitate handling of the valve, the housing may have at least one handle, preferably two diametrically opposed handles, extending radially outwards from the housing. The handles may also be used in breaking the valve into two halves. The seams may either extend through the handles or may be offset from the handles. In case the handles can also be separated into two halves, removal of the valve requires less space during handling.

According to another embodiment of the invention, a clamp is provided that is configured to be disposed around a vascular graft and has a first configuration that allows insertion of a valve's introducer sheath into the vascular graft and a second configuration that allows clamping of the vascular graft against the valve's introducer sheath, when inserted in the vascular graft. The clamp comprises at least one annular body having a first circumferential end and a second circumferential end, the first and second circumferential ends overlapping so as to permit variation of the inner diameter of the annular body between the first and second configurations.

Preferably, the first and second circumferential ends of the annular body have mating tooth structures together forming a ratchet mechanism. In order to actuate the clamp between the first and second configurations, the clamp may have a first handle and a second handle, the first handle extending radially outwards from the annular body near the first circumferential end and the second handle extending radially outwards from the annular body near the second circumferential end, wherein movement of the first and second handles towards each other causes a decrease of the inner diameter of the annular body. The clamp may further comprise a third handle extending radially outwards from the annular body adjacent the first circumferential end and being spaced from the first handle, wherein movement of the first and third handles towards each other causes the first circumferential end to flex radially outwards, thereby allowing release of the ratchet mechanism.

In order to facilitate removal of the clamp, the annular body may include a longitudinal notch forming a predetermined breaking line to allow breaking of the clamp along a longitudinal direction intermediate the first and second circumferential ends. In particular, this facilitates removal of the clamp in case a medical device, such as a catheter, is inserted through the vascular graft. Preferably, the notch is disposed in the annular body opposite the ratchet mechanism.

The clamp may comprise at least two of said annular bodies joined together magnetically, mechanically, physically or chemically to form a single integral body. This is particularly useful when a stack of successive valves is used as described in detail hereinafter. A circumferential notch may be circumferentially disposed between the at least two annular bodies to form a predetermined breaking line, thereby allowing separation of the annular bodies.

According to another embodiment of the invention, a kit for use with a vascular graft is provided. The kit comprises at least one valve comprising a housing, the housing including a flexible membrane having at least one of a passage extending through the membrane and a weakened area to allow a medical device to be inserted through the membrane. The valve further comprises an introducer sheath configured to be inserted into an open end of a tubular body of a vascular graft. The kit further comprises at least one clamp configured to be disposed around the graft's tubular body and having a first configuration that allows insertion of the valve's introducer sheath into the open end of the graft's tubular body and a second configuration that allows clamping of the graft against the valve's introducer sheath when inserted in the graft's tubular body. Preferably, the at least one valve and/or the at least one clamp are constructed as described above.

According to another embodiment of the invention a system is provided that comprises at least two of the aforementioned valves, wherein the introducer sheath of one of the at least two valves is connectable to the respective other one of the at least two valves, preferably connectable to a distal end of the respective other one of the at least two valves so as to be attachable in series at the distal end of the vascular graft. Preferably, the introducer sheath of said one of the at least two valves is configured to be inserted into the housing of said other one of the at least two valves. The system may also comprise a vascular graft. A stack of successive valves further improves hemostasis by providing a double or multiple safety feature against blood leakage.

In a preferred embodiment, each of the at least two valves has a membrane with a central hole, wherein the diameter of the central hole and/or the size of the at least one passage increases from one valve to a respective subsequent valve in a direction towards the graft. The different sizes may be adapted to different medical devices to be inserted, such as a guide wire (K-wire) and a catheter.

A system may be provided wherein the introducer sheath of at least one of the at least two valves has a length that is at least ten times the diameter of said introducer sheath. Such elongate introducer sheath is particularly useful in case a medical device, such as a catheter pump, is to be received in the introducer sheath, e.g. pre-mounted.

The system comprising at least two valves may further comprise at least two clamps constructed as described in the aforementioned, wherein at least one of the clamps is configured to be disposed around the housing of one of the valves. The at least one clamp may be used to close a valve by radially compressing its membrane. The at least two clamps may be joined together by magnetic, mechanic or physical forces. One extra clamp may be needed to clamp the system to the graft, or one clamp of the two clamps is designed to clamp around the graft and around at least one of the valves simultaneously or in a separate fashion.

In a preferred embodiment, the medical device is a catheter. The medical device may comprise an axial blood pump arranged at the tip of the catheter to provide a ventricular assist device.

According to still another embodiment of the invention a system for providing vascular access in a patient's body is provided. The system comprises a vascular graft comprising a tubular body having a proximal end and a distal end, the proximal end being configured to be attached to a vessel in a patient's body. The system further comprises at least one clamp configured to be disposed around the tubular body of the graft and having a first configuration that allows insertion of a valve's introducer sheath into the distal end of the graft's tubular body and a second configuration that allows clamping of the graft against the valve's introducer sheath when inserted in the graft's tubular body. The at least one clamp may be constructed as described in the aforementioned. The system may further comprise at least one valve that may be constructed as described in the aforementioned.

BRIEF DESCRIPTION OF THE DRAWINGS

The foregoing summary, as well as the following detailed description of preferred embodiments, are better understood when read in conjunction with the appended drawings. For the purpose of illustrating the present disclosure, reference is made to the drawings. The scope of the disclosure is not limited, however, to the specific embodiments disclosed in the drawings. In the drawings.

DETAILED DESCRIPTION

Figure 1:
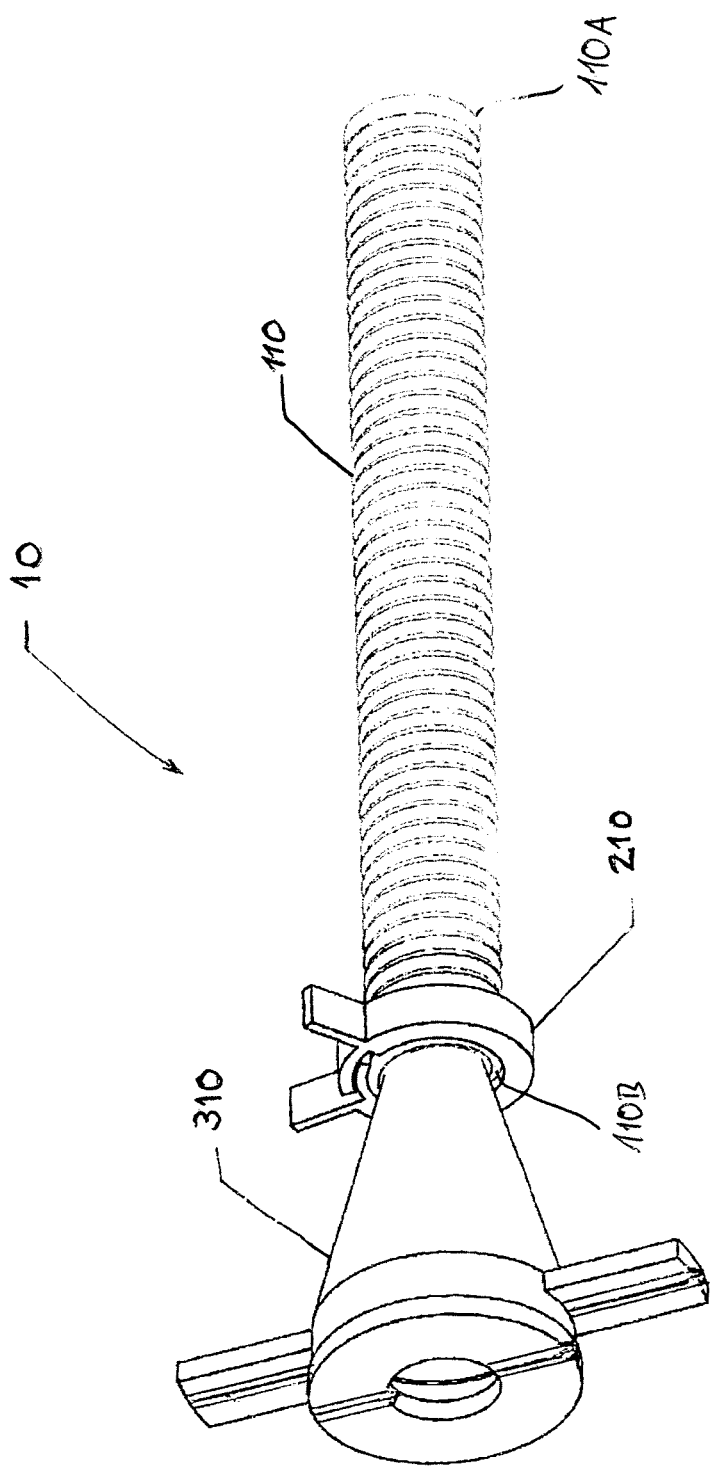
FIG. 1 shows a general view of disclosed graft system.
Figure 2:
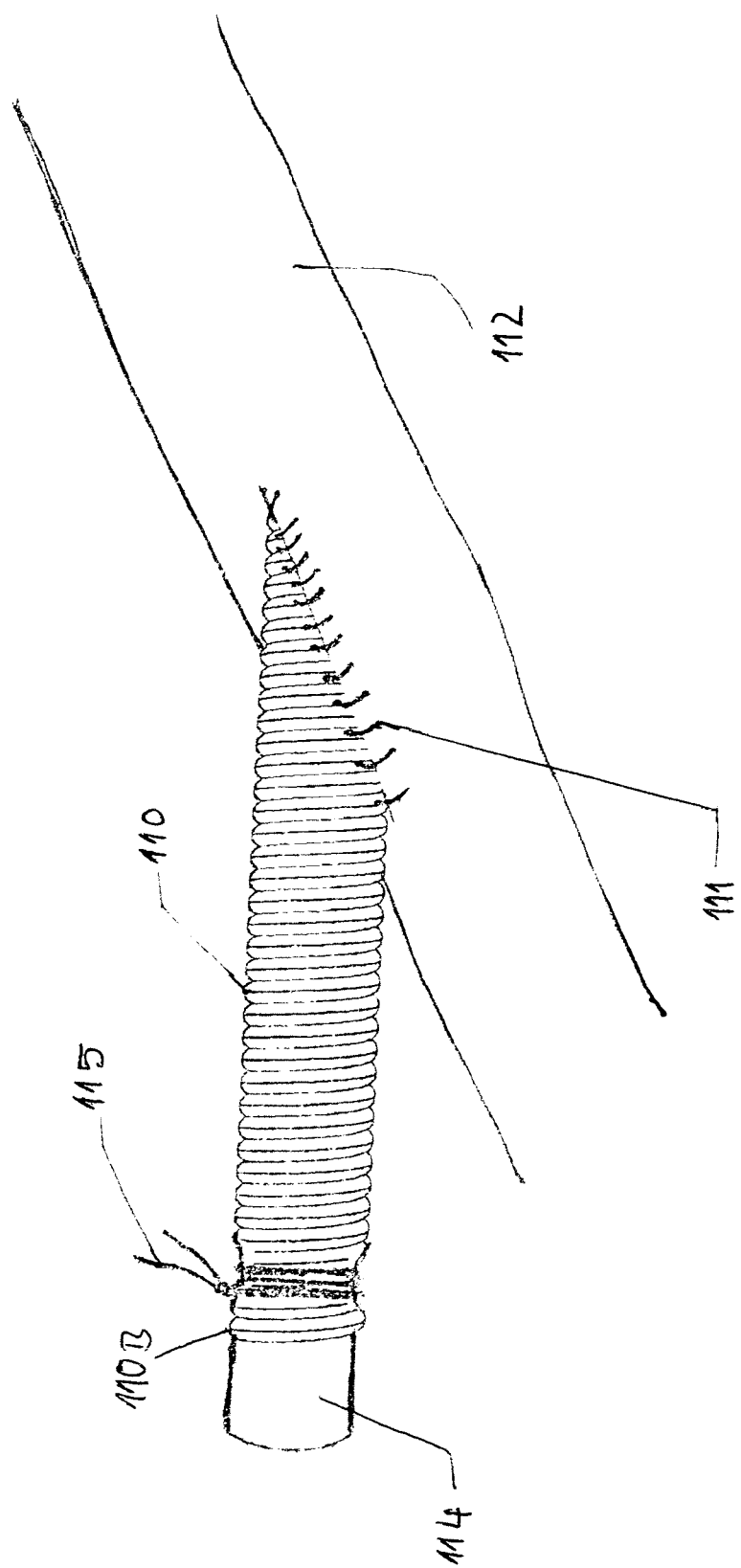
FIG. 2 shows a prior art vascular graft anastomosed to a vessel.

Referring to FIG. 1, a graft system 10 in accordance with the present invention is shown. The graft system 10 comprises a graft 110 having a proximal end 110A and a distal end 110B, a clamp 210 and a hemostasis valve 310. The graft 110 is typically a porous soft medical fabric as described in U.S. Pat. No. 3,953,566 and is intended for use as a conduit in contact with blood and biological tissue. The graft 110 is a commonly used medical product available in many different shapes, sizes and materials. The graft 110 is typically sutured to a vessel as shown in FIG. 2 wherein the graft 110 is secured to vessel 112 using surgical sutures 111. Sutures 111 are common medical products available in many different shapes, sizes and materials.

Typically, a graft 110 is used in a medical procedure that needs to gain access to a vessel in order to introduce and/or remove a medical product and/or devices, or to allow blood or bodily fluid to be circulated through the graft 110 to other parts of the vasculature or to the outside. In the case that the graft 110 is used to introduce a medical device 114, the graft's proximal end 110B is typically occluded using a medical thread 115 wrapped around the graft 110 and knotted as shown in FIG. 2. However, securing a medical device 114 using a medical thread 115 is not very reproducible and leads to blood loss during the time it is implemented.

Referring back to FIG. 1, the graft system 10 shows the use of the hemostasis valve 310 and the clamp 210 to allow the introduction of a medical device without the risk of blood loss. The clamp 210 basically eliminates the need to use a medical thread 115 and eliminates the subjectivity of the procedure, leading to immediate hemostasis and a more reproducible outcome.

Figure 3:
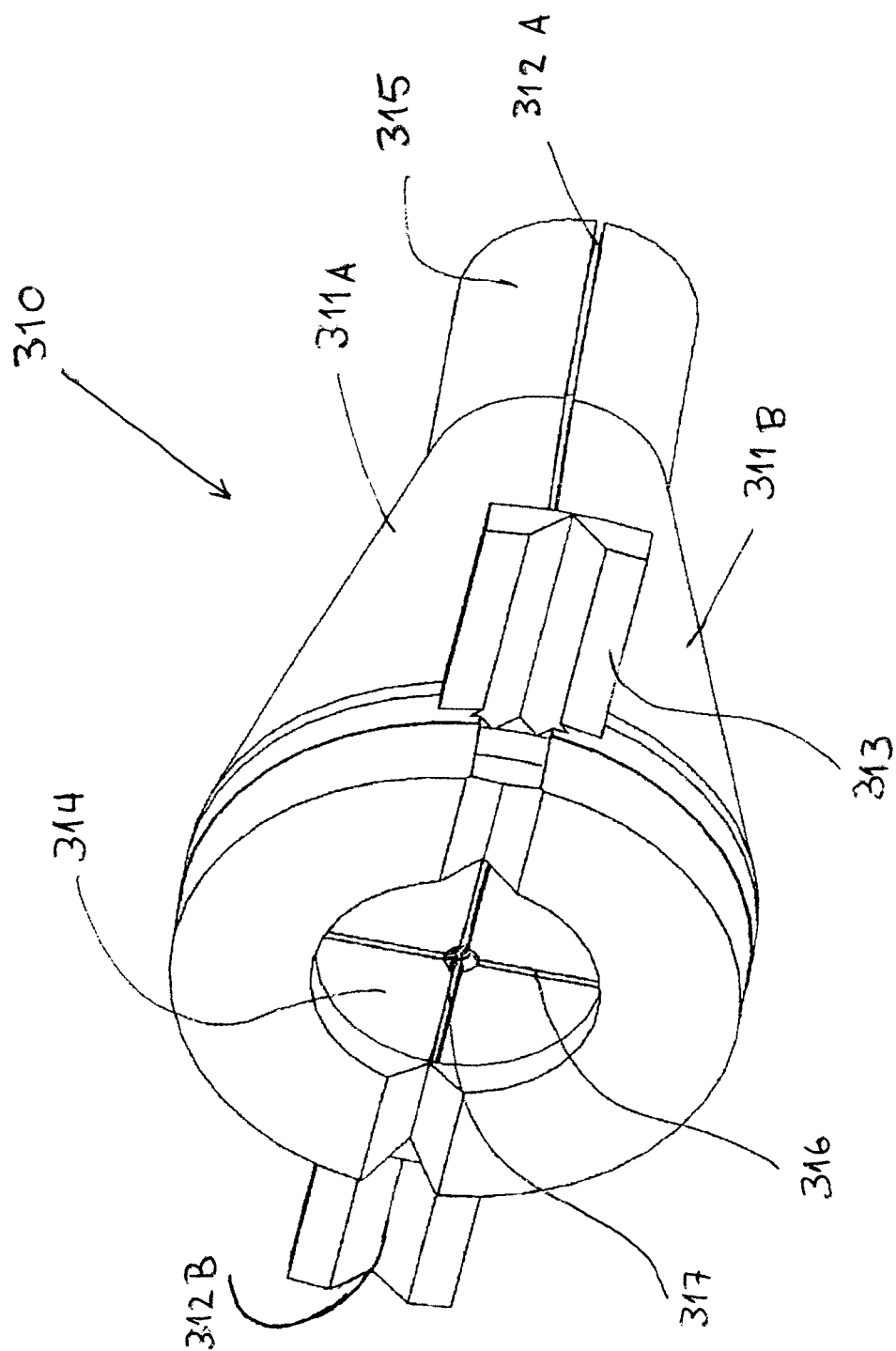
FIG. 3 shows details of a hemostasis valve.

Referring to FIG. 3, an embodiment of the hemostasis valve 310 in accordance with the present invention is shown. The hemostasis valve 310 comprises a slit membrane 314, an introducer sheath 315 and a housing 311. The housing 311 comprises two distinct halves 311A, 311B joined by two seams 312A, 312B that travel the entire length of the hemostasis valve 310. The seams 312A, 312B are intended to thin the wall of the hemostasis valve 310 to provide a preferential breaking line in the event that the hemostasis valve 310 is split in two halves resulting in two separate halves 311A, 312B. Handles 313 are intended to assist the user in handling the hemostasis valve 310 as well as providing a handle to assist in separating the hemostasis valve 310 into two separate halves. In this embodiment, seams 312A, 312B travel the middle of the handles 313 in order to facilitate breaking the handles 313 into two halves.

The slit membrane 314 is typically a soft rubber disk that comprises membrane slits 316 and a center hole 317 to ease the introduction or removal of any device through the hemostasis valve 310. Some or all of the slits 316 and the center hole 317 extend through the entire thickness of the slit membrane 314 or partially through the slit membrane 314 for a portion or the entire length of the slits 316 to ease any device introduction through the slit membrane 314 or to allow easy separation of the slit membrane 314 into separate pieces. A minimum of one slit or a multitude of slits may be included depending on the intended use of the valve. Similarly, the length of the slits 316 may vary according to the intended use. For example, a hemostasis valve intended to be used in association with a large diameter device would typically have longer membrane slits 316 as well as a larger diameter center hole 317.

The introducer sheath 315 is typically a thin walled tubular component that is inserted into the graft 110 and secured in place with the clamp 210.

Figure 4:
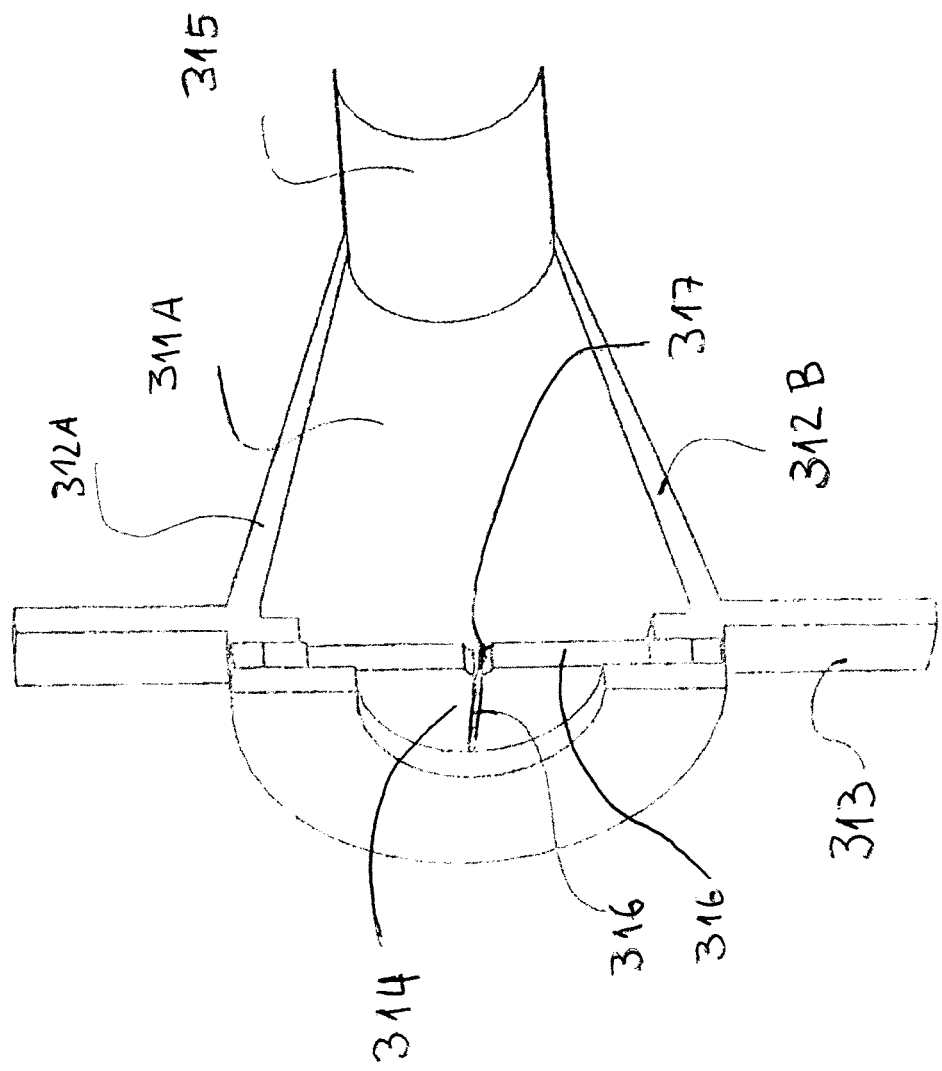
FIG. 4 shows a section view of the hemostasis valve along a seam.

FIG. 4 shows a section view of the hemostasis valve 310, wherein the introducer sheath 315, the hemostasis valve half 311A and the slit membrane 314 have been separated from their mating halves.

Figure 5:
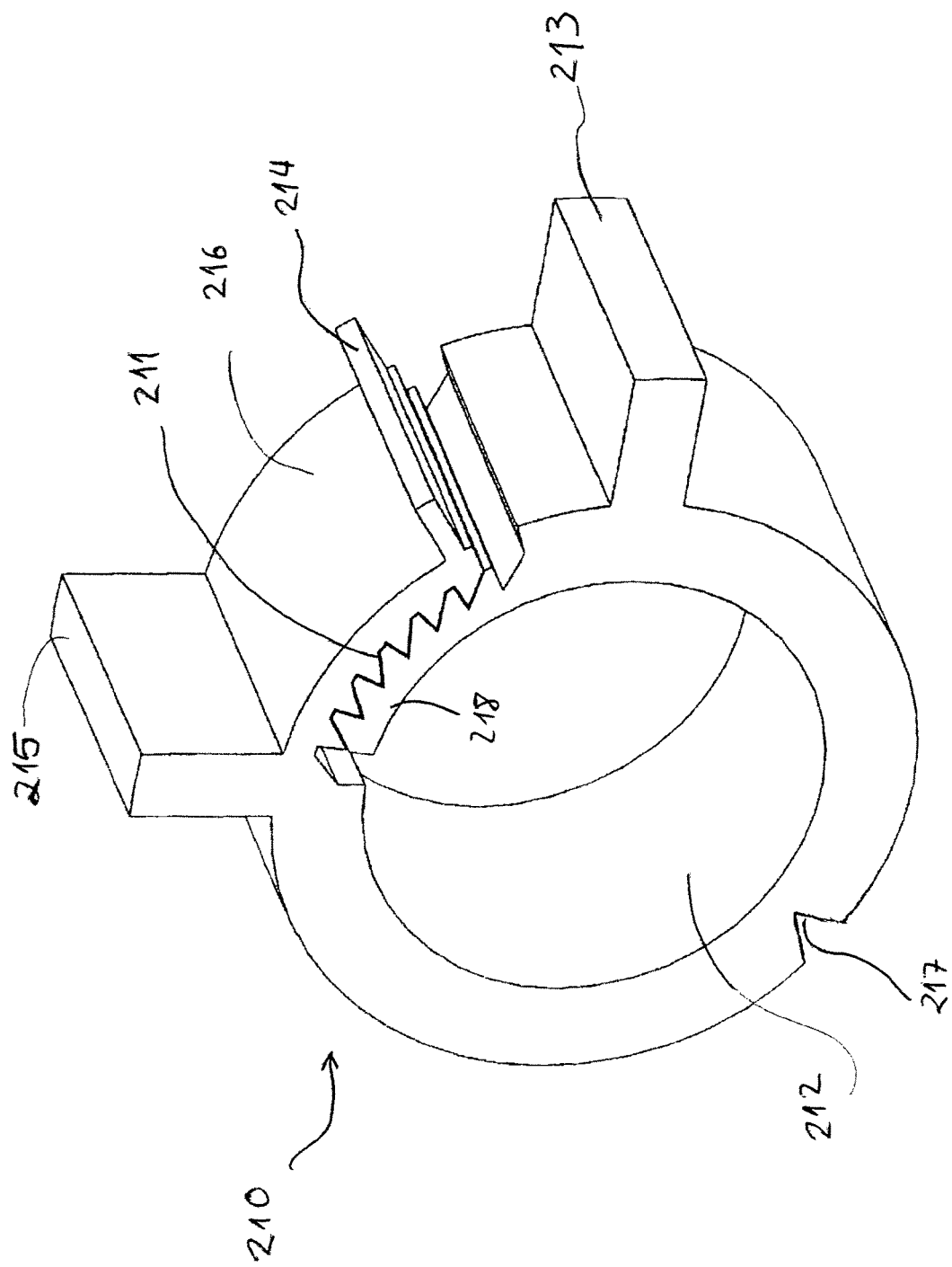
FIG. 5 shows details of a clamp.

Referring to FIG. 5, the clamp 210 comprises an annular body with first and second overlapping circumferential ends 216, 218 and a toothed structure 211, in particular a ratchet mechanism, to allow maintaining of a clamped position of an inner surface 212 on any circular structure positioned inside the clamp 210 and in contact with the inner surface 212. A compressing handle 213 and a release handle 214 will decrease the diameter of the inner surface 212 and move the toothed structure 211 in a direction that will cause the toothed structure 211 to lock and maintain a tighter compression on any circular structure passing through the clamp 210. Conversely, compressing an unlock handle 215 and the release handle 214 will cause disengagement of the toothed structure 211 and release any compression force on any circular structure in contact with the inner surface 212. Preferably, the first circumferential end comprises a release band 216, situated between the unlock handle 215 and the release handle 214, which is made from a soft pliable material to facilitate engagement and disengagement of the toothed structure 212. In addition, a softer release band 216 will allow a softer grip on any circular structure positioned inside the clamp 210. A notch 217 is provided as a longitudinal thinning of the wall of the clamp 210. The notch 217 creates a weak area preferably along the entire length of the clamp 210 to allow breaking of the clamp 210 into two separate pieces and easy removal of the clamp 210 in case it is not needed any further. In case the clamp 210 is not intended to be removed from use, the notch 217 may be eliminated from the clamp 210.

Figure 6:
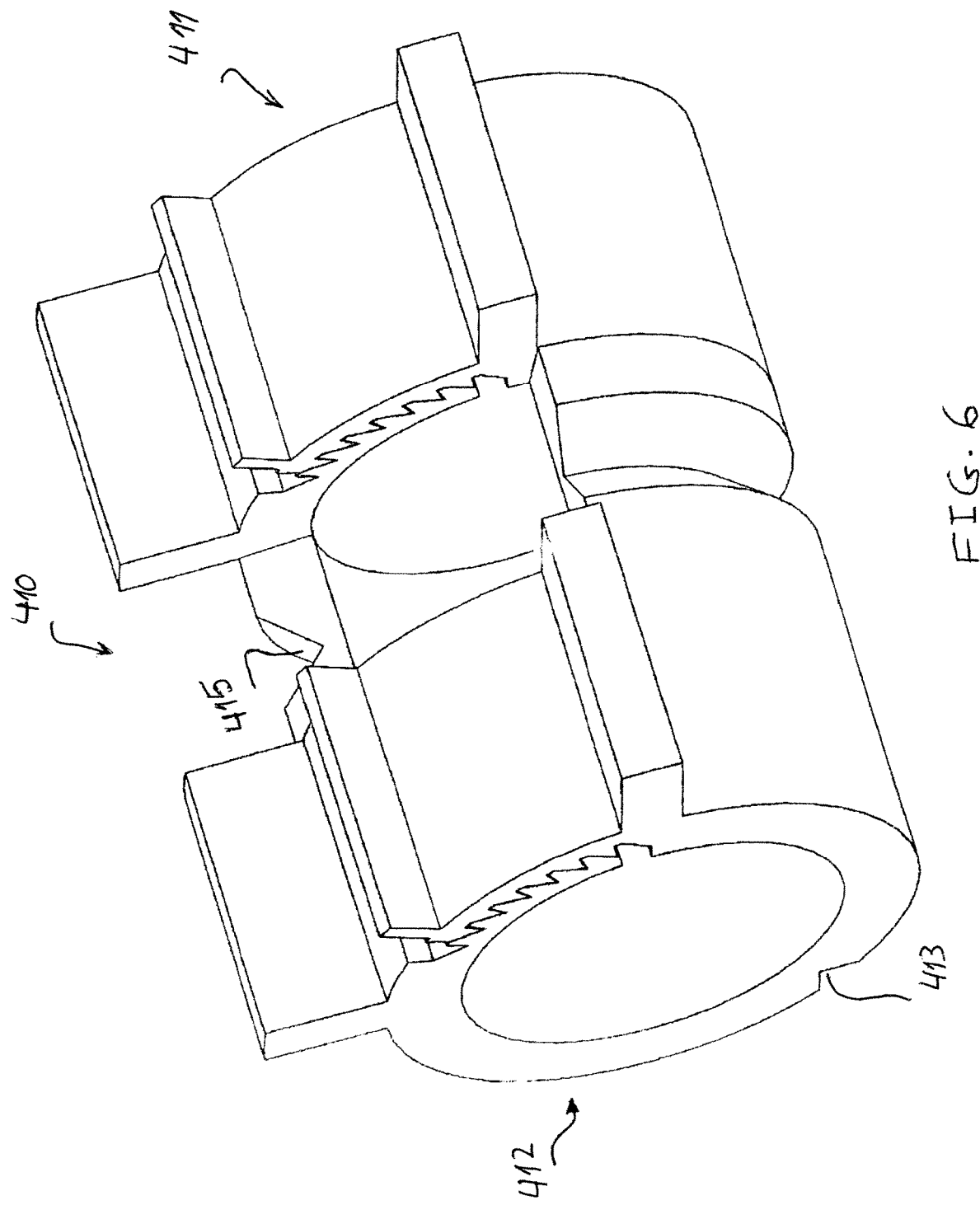
FIG. 6 shows details of a dual clamp.

Referring to FIG. 6, another embodiment in accordance with the present invention shows a dual clamp 410, wherein the dual clamp 410 comprises a dual clamping mechanism, a proximal clamp 411 and a distal clamp 412, which can act separately or as a single clamp. The proximal clamp 411 and the distal clamp 412 may be constructed as a single component or may be constructed as separate components that are joined together by a user. The dual clamp 410 may comprise multiple individual clamps, preferably two to six clamps in total. The multitude of clamps may be constructed as a single component or as individual clamps that are joined together by a user. The mechanism to join multiple individual clamps (not shown) may be of a magnetic, mechanical, chemical or physical (e.g. adhesive) nature that leads to securing of the multiple clamps to each other. The proximal clamp 411 and the distal clamp 412 may have similar or different features (such as different inner clamp diameter, different maximal clamping force, different material to allow soft or solid clamping on devices passing through the inner diameter) and a similar or different structure compared to the clamp 210 in order to allow versatile use of different devices while maintaining hemostasis. A radial notch 415 is provided to weaken the joining portion of the proximal clamp 411 and the distal clamp 412 in order to allow the proximal clamp 411 and the distal clamp 412 to be broken apart when desired. A longitudinal notch 413 is provided to weaken the distal clamp 412 to allow breaking of the distal clamp 412 along a longitudinal direction and allow the removal of the distal clamp 412. The proximal clamp 411 may have a similar notch (not shown) for the same purpose.

Figure 7:
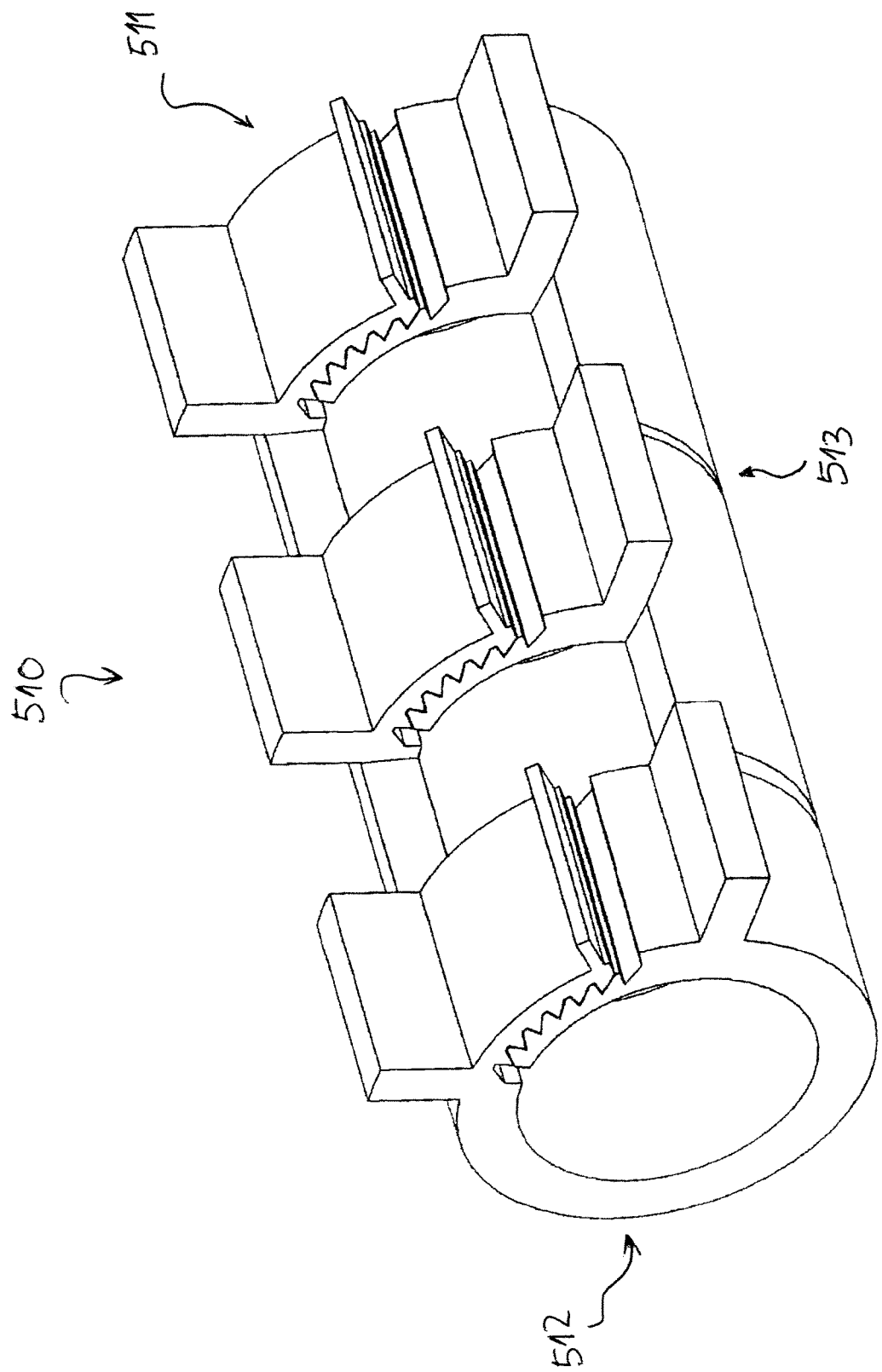
FIG. 7 shows details of a multiple clamp.

Referring to FIG. 7, another embodiment of the clamping mechanism in accordance with the present invention is shown wherein multiple clamp 510 comprises a triple clamping mechanism proximal clamp 511, a triple clamping mechanism distal middle clamp 513 and a triple clamping mechanism distal clamp 512 that can act separately or as a single clamp. The triple clamping mechanism proximal clamp 511, the triple clamping mechanism distal middle clamp 513 and the triple clamping mechanism distal clamp 512 may be constructed as a single component or may be constructed as separate components that are joined together by a user. The multiple clamp 510 may comprise multiple individual clamps, preferably two to six clamps in total. The multitude of clamps may be constructed as a single component or as individual clamps that are joined together by a user. The mechanism to join multiple individual clamps (not shown) may be of a magnetic, mechanical, chemical or physical (e.g. adhesive) nature that leads to securing of the multiple clamps to each other. The triple clamping mechanism proximal clamp 511, the triple clamping mechanism distal middle clamp 513 and the triple clamping mechanism distal clamp 512 may have similar or different features (such as different inner clamp diameter, different maximal clamping force, different material to allow soft or solid clamping on devices passing through the inner diameter) and a similar or different structure compared to the clamp 210 in order to allow versatile use of different devices while maintaining hemostasis.

Figure 8:
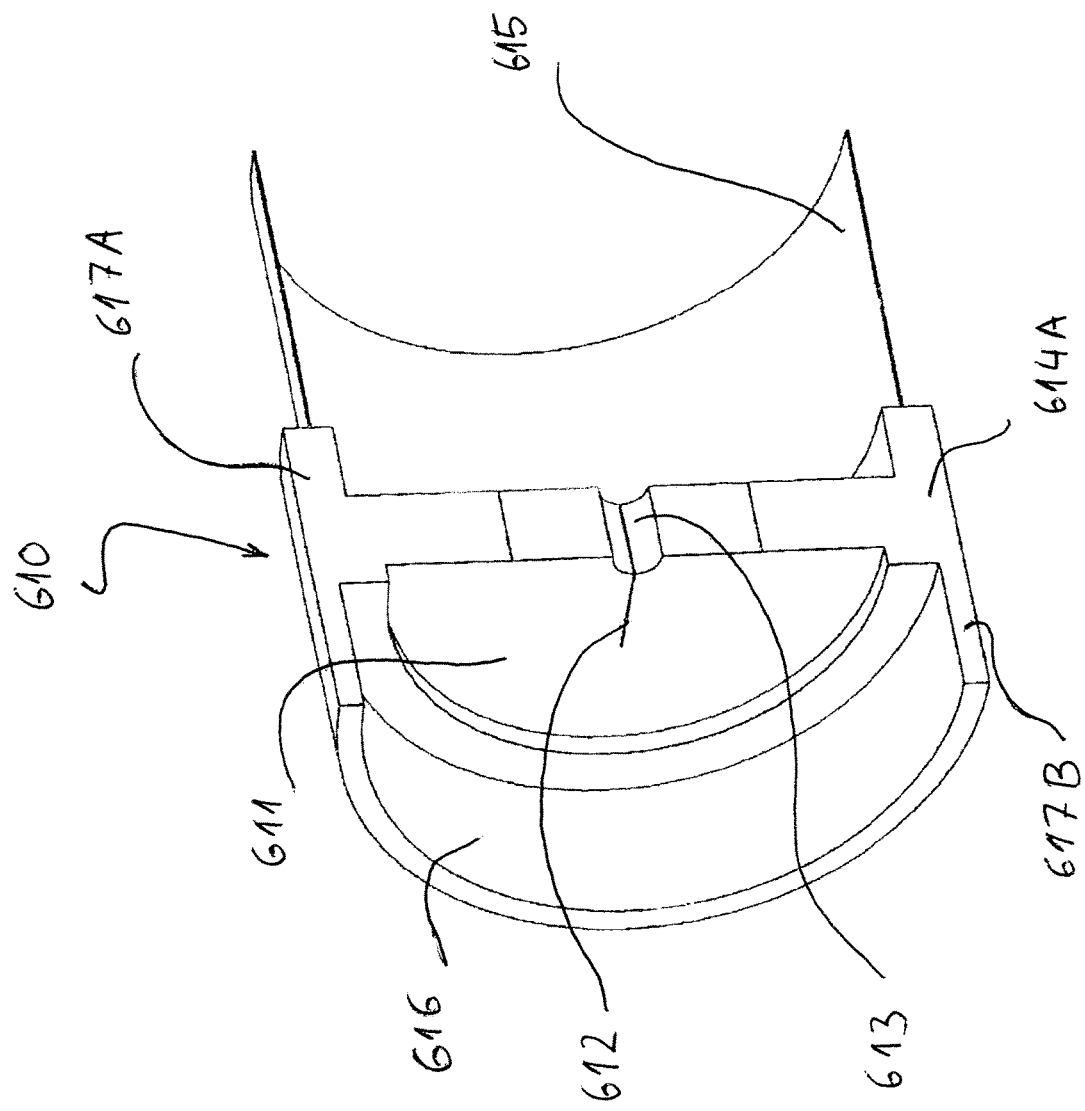
FIG. 8 shows details of a low profile hemostasis valve.

Now referring to FIG. 8, another embodiment of the hemostasis valve in accordance with the present invention is shown in cross section wherein the low profile hemostasis valve 610 comprises a slit membrane 611, an introducer sheath 615 and a housing 616. The housing 616 comprises two distinct halves, where one of the halves is shown and indicated as 614A (the other half 614B is not shown), joined by two seams 617A, 617B that travel preferably the entire length of the low profile hemostasis valve 610. The seams 617A, 617B are intended to thin the wall of the low profile hemostasis valve 610 to provide a preferential breaking line in the event that the low profile hemostasis valve 610 needs to be split in two halves resulting in two separate halves 614A, 614B. A portion or the entire body of the housing 616 is preferably made of a soft polymer that allows clamping of the slit membrane 611 when clamped with a clamp, such as clamp 210. The slit membrane 611 is typically a soft rubber disk that comprises membrane slits 612 and a center hole 613 to ease the introduction or removal of any solid device through the low profile hemostasis valve 610. A minimum of one slit or a multitude of slits may be included depending on the intended use of the valve. Similarly, the length of the slits 612 may vary according to the intended use. For example, a hemostasis valve intended to be used in association with a large diameter device would typically have longer membrane slits 612 as well as a larger diameter center hole 613. One or several slits of the slits 612 may extend along the entire diameter of the slit membrane 611 to facilitate separating the membrane into several parts and allow its removal from any device or catheter passing through the center hole 613.

Figure 9:
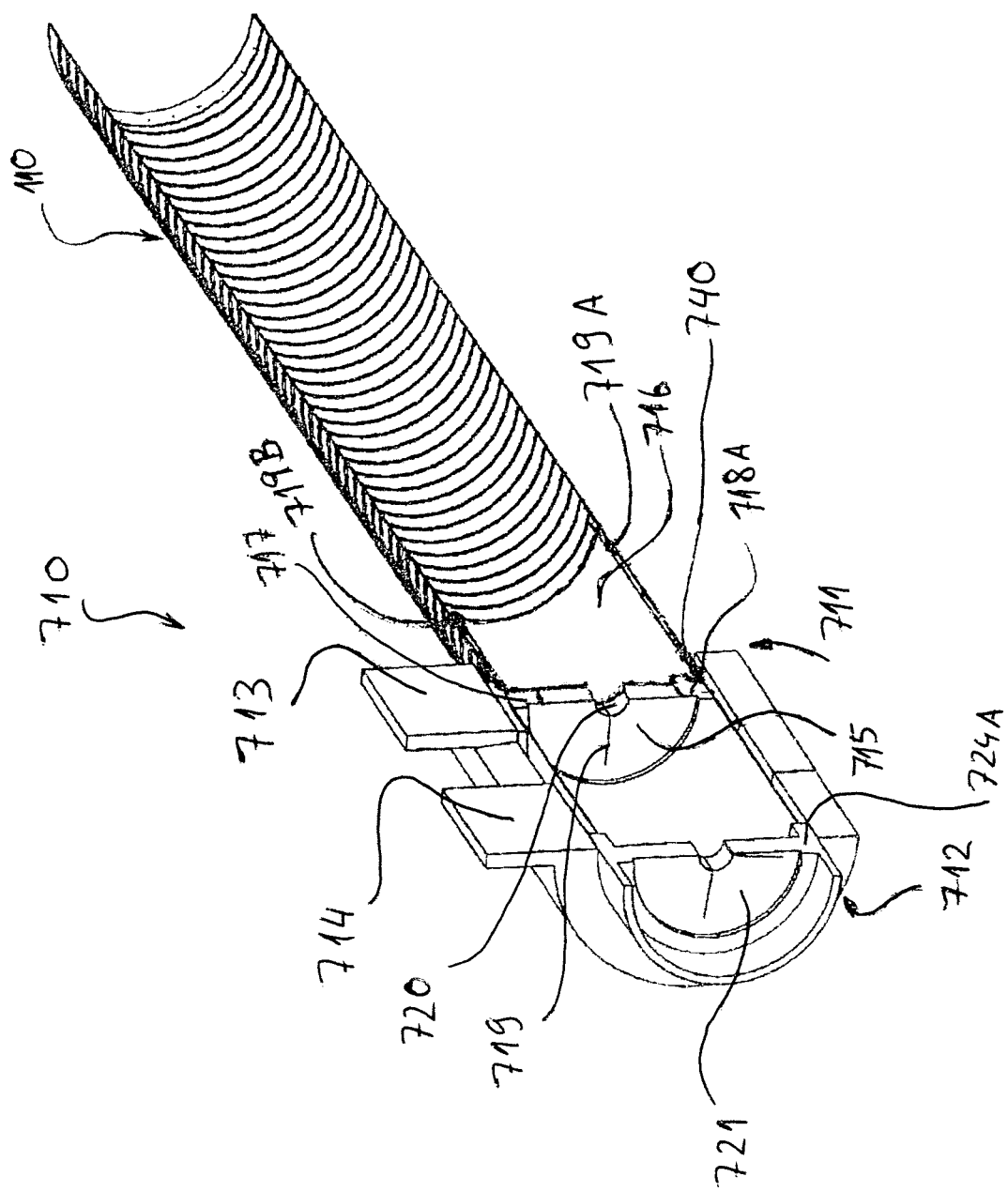
FIG. 9 shows multiple hemostasis valves attached to a graft shown in a section view.
Figure 10:
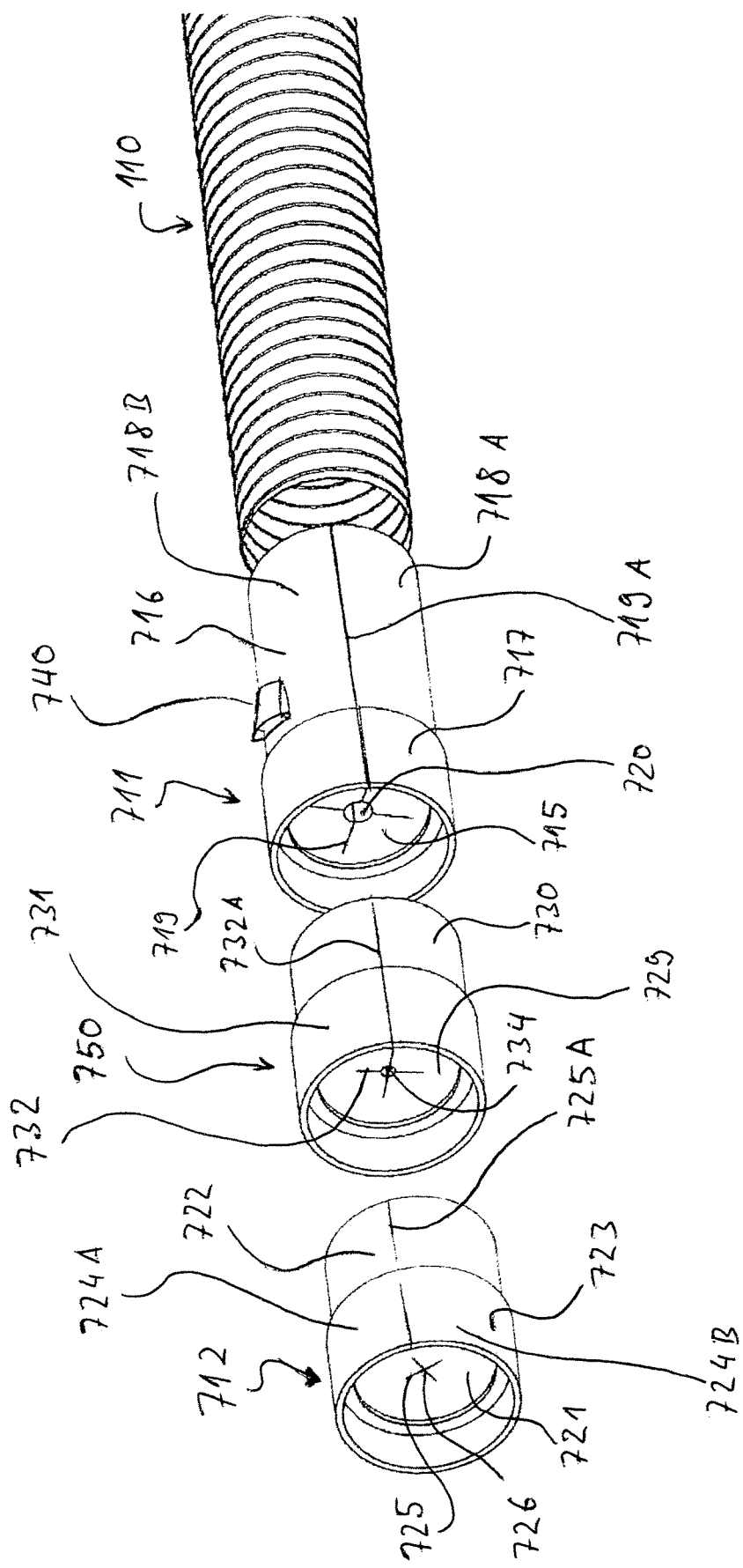
FIG. 10 shows a graft system with multiple hemostasis valves in an exploded view.
Figure 11:
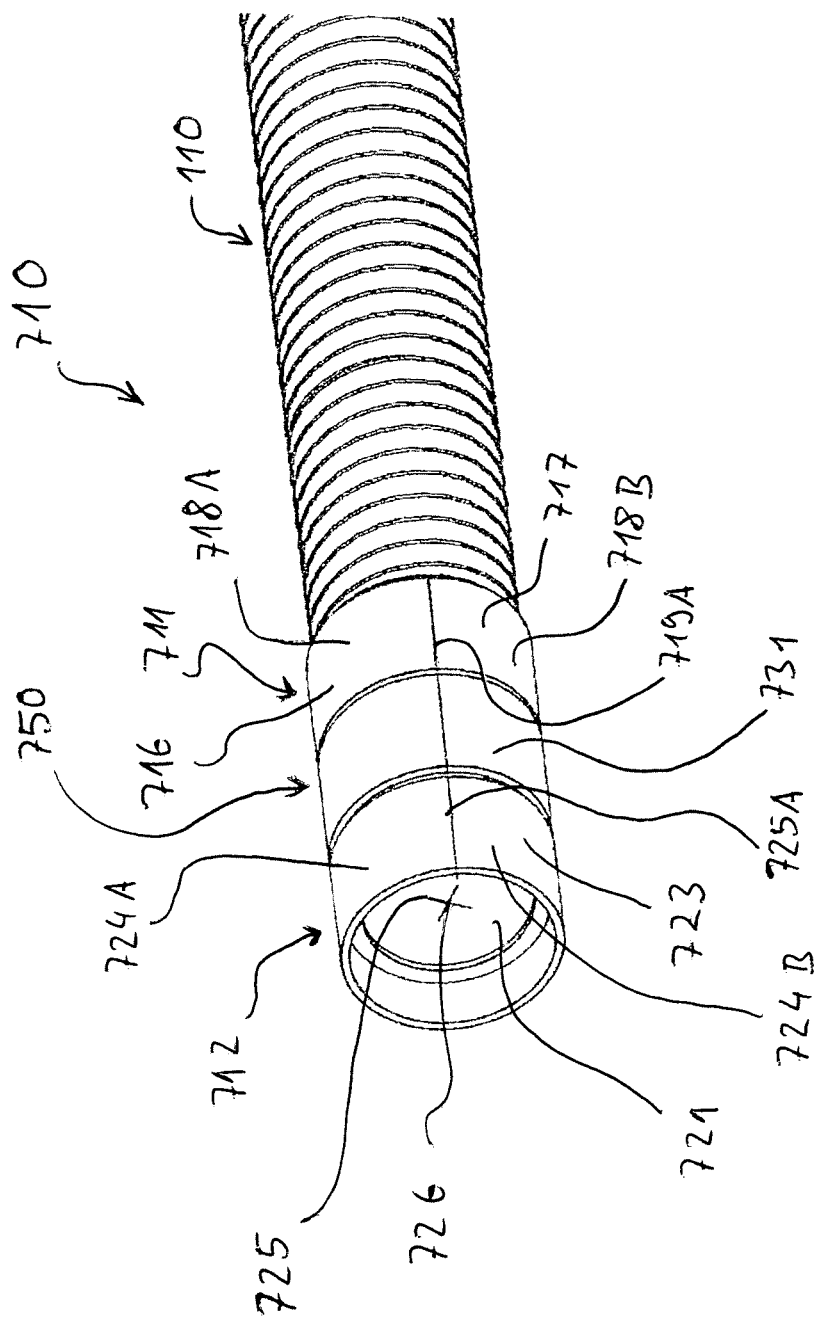
FIG. 11 shows a graft system with multiple hemostasis valves in an assembled view.

Now referring to FIGS. 9, 10 and 11, another embodiment of graft system 710 with multiple hemostasis valves in accordance with the present invention is shown in a section view in FIG. 9, an exploded view in FIG. 10 and an assembled view in FIG. 11. The graft system 710 with multiple hemostasis valves comprises a graft 110, a proximal hemostasis valve 711, a distal hemostasis valve 712, a proximal clamp 713 and a distal clamp 714. The proximal hemostasis valve 711 is similar, to some extent, to the low profile hemostasis valve 610 in feature and function and comprises a proximal hemostasis valve slit membrane 715, a proximal hemostasis valve introducer sheath 716 and a proximal hemostasis valve housing 717. The proximal hemostasis valve housing 717 comprises two distinct halves (whereas one of the halves is shown and indicated as 718A, the other half 718B is not shown in FIG. 9), joined by a proximal hemostasis valve seam 719A and a proximal hemostasis valve seam 719B that travel preferably the entire length of the proximal hemostasis valve 711. The proximal hemostasis valve seams 719A, 719B are intended to thin the wall of the proximal hemostasis valve 711 to provide a preferential breaking line in the event that the proximal hemostasis valve 711 is split in two halves resulting in two separate halves 719A, 719B. A portion or the entire body of the proximal hemostasis valve housing 717 is preferably made of a soft polymer that allows clamping of the proximal hemostasis valve slit membrane 715 when clamped with a clamp, such as proximal clamp 713. The proximal hemostasis valve slit membrane 715 is typically a soft rubber disk that comprises proximal hemostasis valve membrane slits 719 and a proximal hemostasis valve center hole 720 to ease the introduction or removal of any solid device through the proximal hemostasis valve 711. A minimum of one slit or a multitude of slits may be included depending on the intended use of the valve. Similarly, the length of the proximal hemostasis valve slits 719 may vary according to the intended use. For example, a hemostasis valve intended to be used in association with a large diameter device would typically have longer proximal hemostasis valve membrane slits 719 as well as a larger diameter proximal hemostasis valve center hole 720. A barb 740 is provided as a raised surface located on the proximal hemostasis valve introducer sheath 716 to engage the inner surface of the graft 110 and assure a firm grip when the graft 110 is captured between the barb 740 and the proximal clamp 710. The barb 740 may cover a portion or the full circumference of the proximal hemostasis valve introducer sheath 716. The barb 740 may be a single raised surface or multiple raised surfaces radially aligned with or offset from each other to provide greater grip force on the graft 110. The barb 740 may allow the user to tie the proximal hemostasis valve introducer sheath 716 to the graft 110 using sutures, umbilical tape, medical tape or other means. Tying the proximal hemostasis valve introducer sheath 716 to the graft 110 provides a stabilized connection less likely to disconnect or shift during insertion or removal of a device.

The distal hemostasis valve 712 is similar to the low profile hemostasis valve 610 in feature and function and comprises a distal hemostasis valve slit membrane 721, a distal hemostasis valve introducer sheath 722 and a distal hemostasis valve housing 723. The distal hemostasis valve housing 723 comprises two distinct halves (whereas one of the halves is shown and indicated as 724A, the other half 724B is not shown in FIG. 9), joined by a distal hemostasis valve seam 725A and a distal hemostasis valve seam 725B that travel preferably the entire length of the distal hemostasis valve 712. The distal hemostasis valve seams 725A, 725B are intended to thin the wall of distal hemostasis valve 712 to provide a preferential breaking line in the event that the distal hemostasis valve 711 is split in two halves resulting in two separate halves 725A, 725B. A portion or the entire body of the distal hemostasis valve housing 723 is preferably made of a soft polymer that allows clamping of the distal hemostasis valve slit membrane 721 when clamped with a clamp, such as distal clamp 713. The distal hemostasis valve slit membrane 721 is typically a soft rubber disk that comprises distal hemostasis valve membrane slits 725 and a distal hemostasis valve center hole 726 to ease the introduction or removal of any solid device through the distal hemostasis valve 711. A minimum of one slit or a multitude of slits may be included depending on the intended use of the valve. Similarly, the length of the distal hemostasis valve slits 725 may vary according to the intended use. For example, a hemostasis valve intended to be used in association with a large diameter device would typically have longer distal hemostasis valve membrane slits 725 as well as a larger diameter distal hemostasis valve center hole 720.

Now referring to FIG. 10 and FIG. 11, another embodiment of a graft system with multiple hemostasis valves in accordance with the present invention comprises a proximal hemostasis valve 711, a distal hemostasis valve 712 and an intermediate hemostasis valve 750. The intermediate hemostasis valve 750 is similar, to some extent, to the low profile hemostasis valve 610 in feature and function and comprises an intermediate hemostasis valve slit membrane 729, an intermediate hemostasis valve introducer sheath 730 and an intermediate hemostasis valve housing 731. The intermediate hemostasis valve housing 731 comprises two distinct halves joined by an intermediate hemostasis valve seam 732A and an intermediate hemostasis valve seam 732B (not shown in FIG. 10 and FIG. 11) that travel preferably the entire length of the intermediate hemostasis valve 750. The intermediate hemostasis valve seams 732A, 732B are intended to thin the wall of intermediate hemostasis valve 750 to provide a preferential breaking line in the event that the intermediate hemostasis valve 750 is split in two halves resulting in two separate halves 732A, 732B. A portion or the entire body of the intermediate hemostasis valve housing 731 is preferably made of a soft polymer that allows clamping of the intermediate hemostasis valve slit membrane 729 when clamped with a clamp, such as proximal clamp 713. The intermediate hemostasis valve slit membrane 729 is typically a soft rubber disk and comprises intermediate hemostasis valve membrane slits 732 and an intermediate hemostasis valve center hole 734 to ease the introduction or removal of any solid device through the intermediate hemostasis valve 750. A minimum of one slit or a multitude of slits may be included depending on the intended use of the valve. Similarly, the length of the intermediate hemostasis valve slits 732 may vary according to the intended use. For example, a hemostasis valve intended to be used in association with a large diameter device would typically have longer intermediate hemostasis valve membrane slits 732 as well as a larger diameter intermediate hemostasis valve center hole 734. It is to be understood that the slits 719, 732, 725 may have the same length, in particular a maximum length, in order to allow a medical device having a certain diameter to pass through all of the membranes 715, 729, 721, while providing a blood tight connection all the time.

Figure 12:
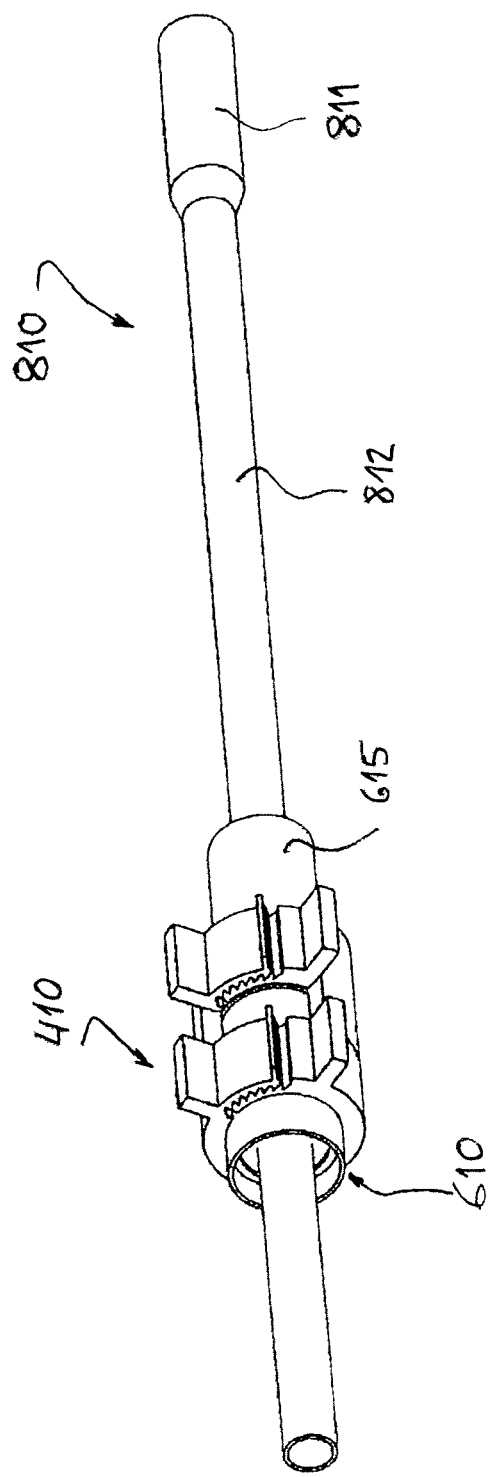
FIG. 12 shows the dual clamp and low profile hemostasis valve mounted on a catheter.

Now referring to FIG. 12, in accordance with the present invention the dual clamp 410 and the low profile hemostasis valve 610 are shown mounted on a catheter 810. The catheter 810 is a general medical catheter intended to be inserted into a vessel or into a cavity of the human body. A functional catheter tip 811 is the functional portion of the catheter that performs a specific function inside the human body and is advanced into the human body by means of a catheter shaft 812 that is advanced inside the human body or a vessel. The catheter 810 is advanced through the low profile hemostasis valve 610 while the dual clamp 410 is released and not exerting any radial force on the low profile hemostasis valve 610. The functional tip 811 may be larger or smaller in diameter than the shaft 812, and the dual clamp 410 may be mounted on the catheter 810 from its distal end or may be pre-mounted on the catheter 810 during manufacture of the catheter 810.

Figure 13:
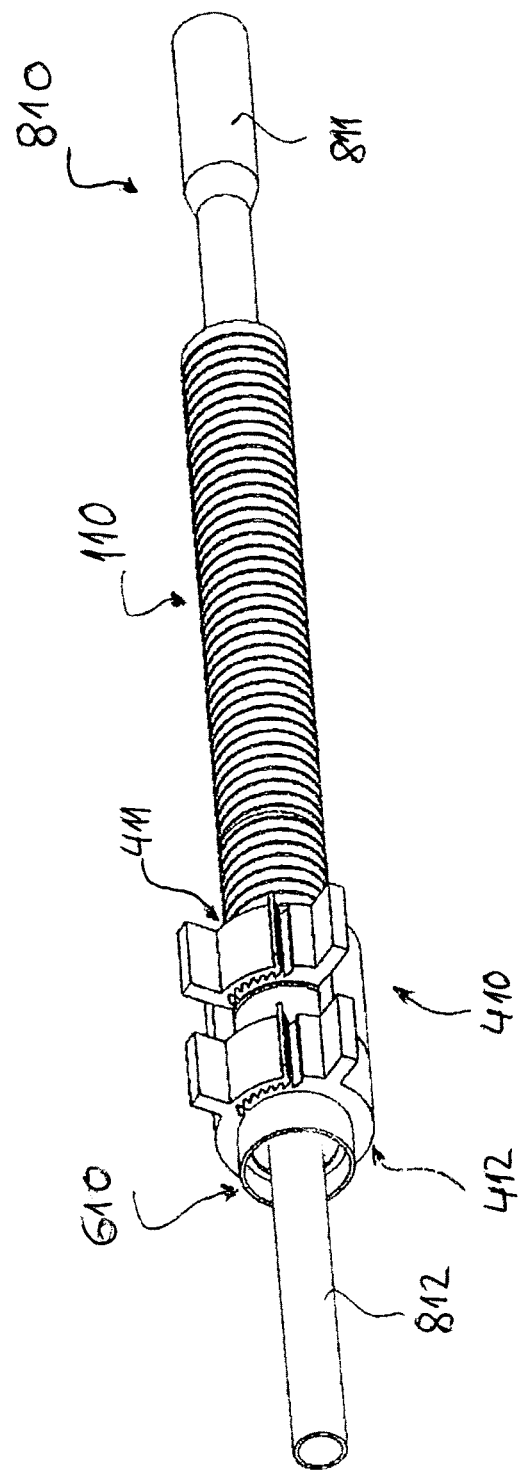
FIG. 13 shows the dual clamp, low profile hemostasis valve, catheter and graft in an assembled view.
Figure 14:
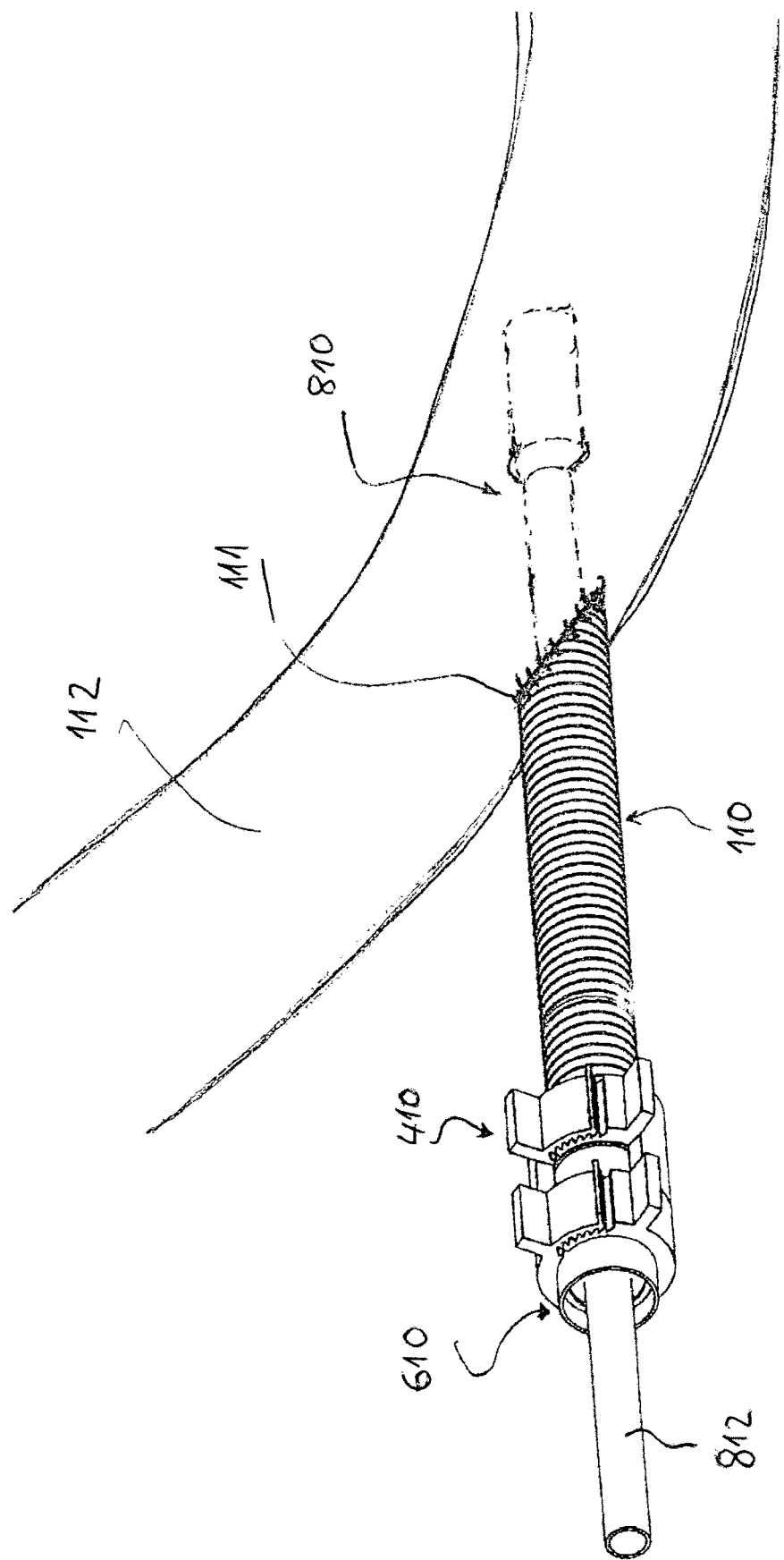
FIG. 14 shows the dual clamp, low profile hemostasis valve, catheter and graft in an assembled view and anastomosed to a vessel.

Now referring to FIG. 13 and FIG. 14, the dual clamp 410, the low profile hemostasis valve 610 and the catheter 810 may be joined to the graft 110 by inserting the catheter 810 and the introducer sheath 615 into the graft 110, and secured in place by clamping the proximal clamp 411 to firmly secure the graft 110 to the proximal clamp 411 and create a hemostasis seal between the graft 110 and the introducer sheath 615. The catheter 810 may be moved forward into the graft 110 by sliding the catheter shaft 812 through the low profile hemostasis valve 610. Clamping the distal clamp 412 will secure the catheter 810 in place and form a hemostasis seal around the catheter shaft 812. In turn, the graft 110 may be anastomosed to a body cavity or vessel 112 (as shown in FIG. 14) by means of surgical sutures 111 or any other anastomotic devices used in medical procedures meant to anastomose a graft to a body cavity or vessel.

Figure 15:
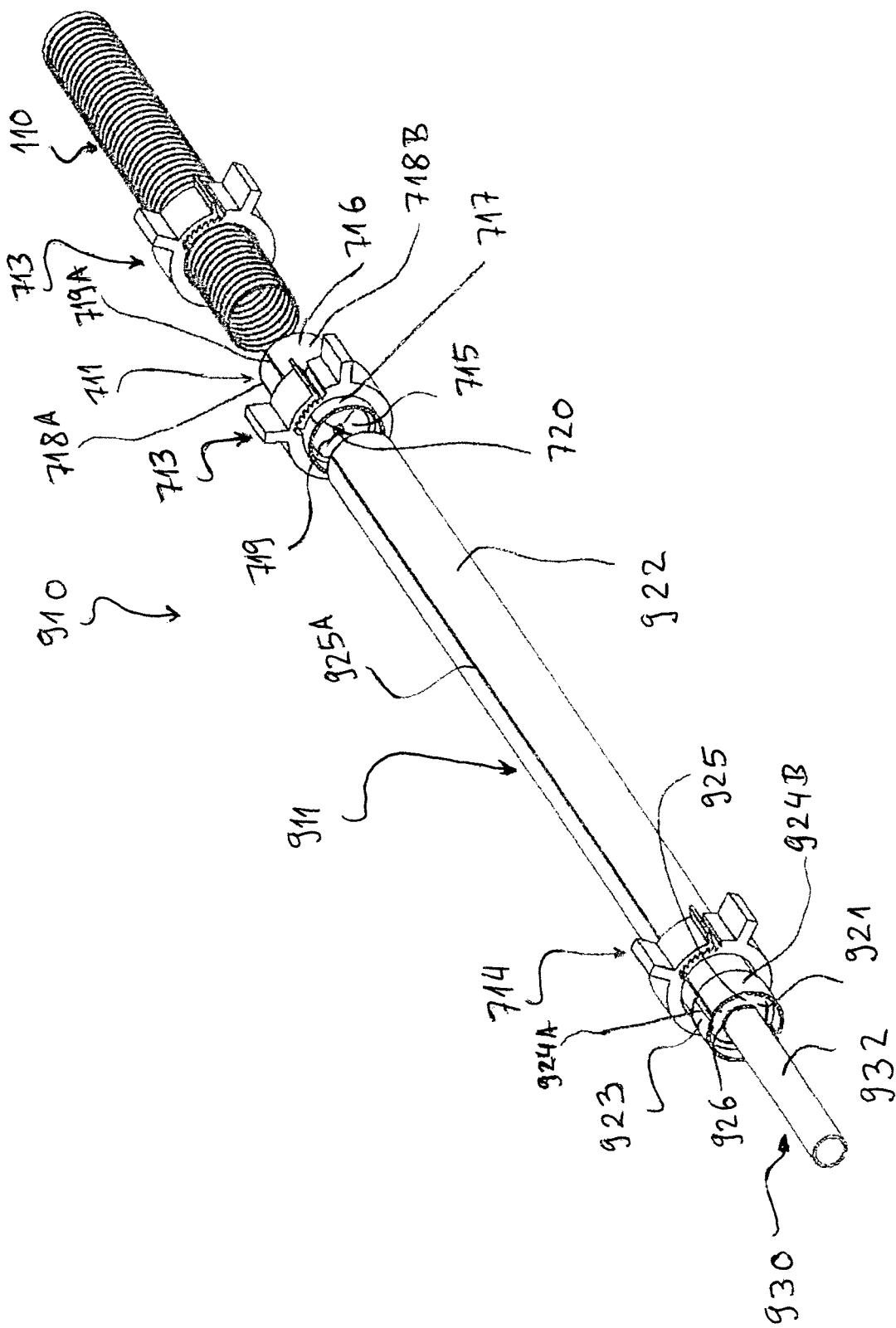
FIG. 15 shows a long introducer sleeve in use with a long device in an exploded view.
Figure 16:
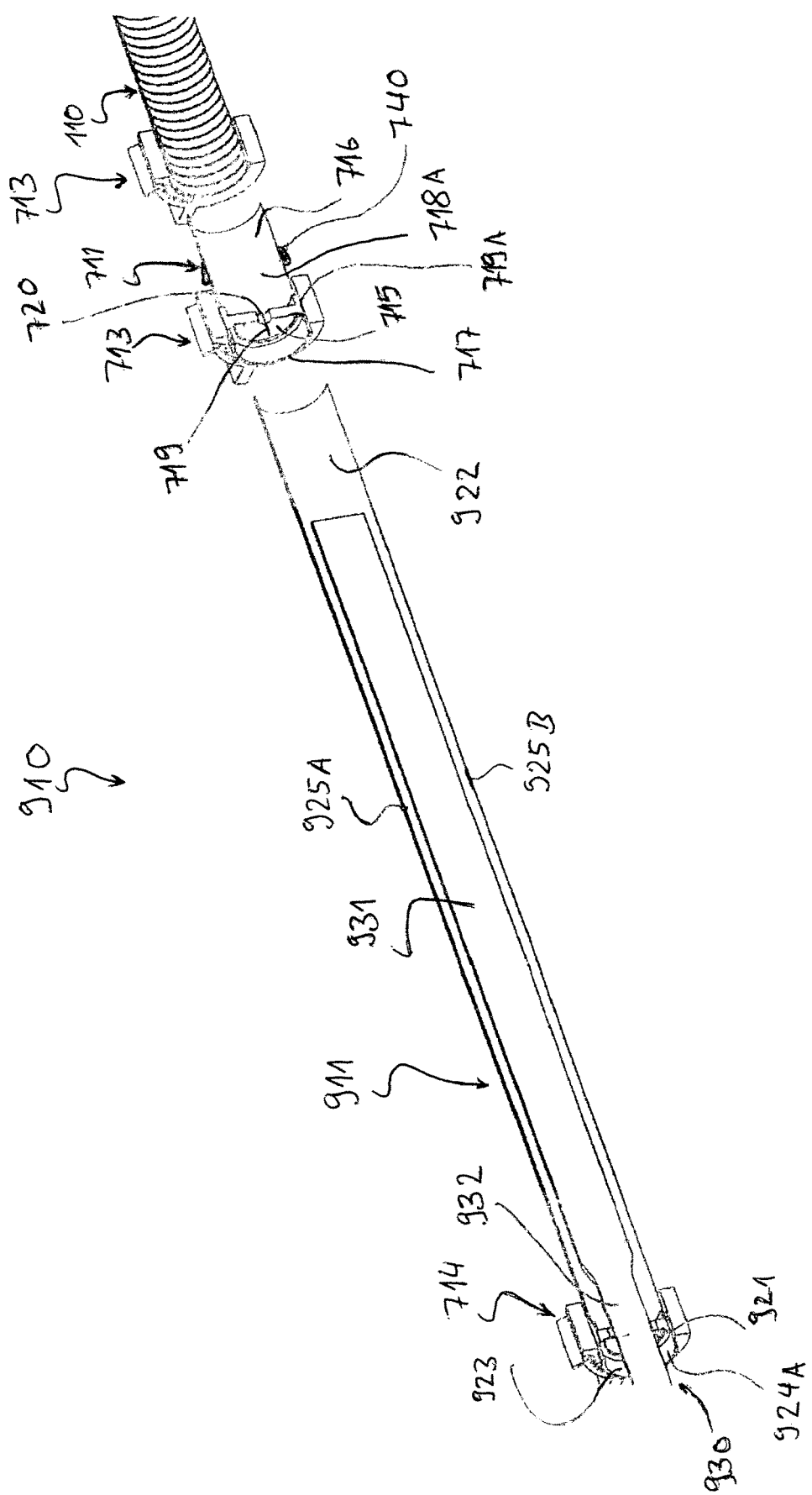
FIG. 16 shows a long introducer sleeve in use with a long device in a section view.
Figure 17:
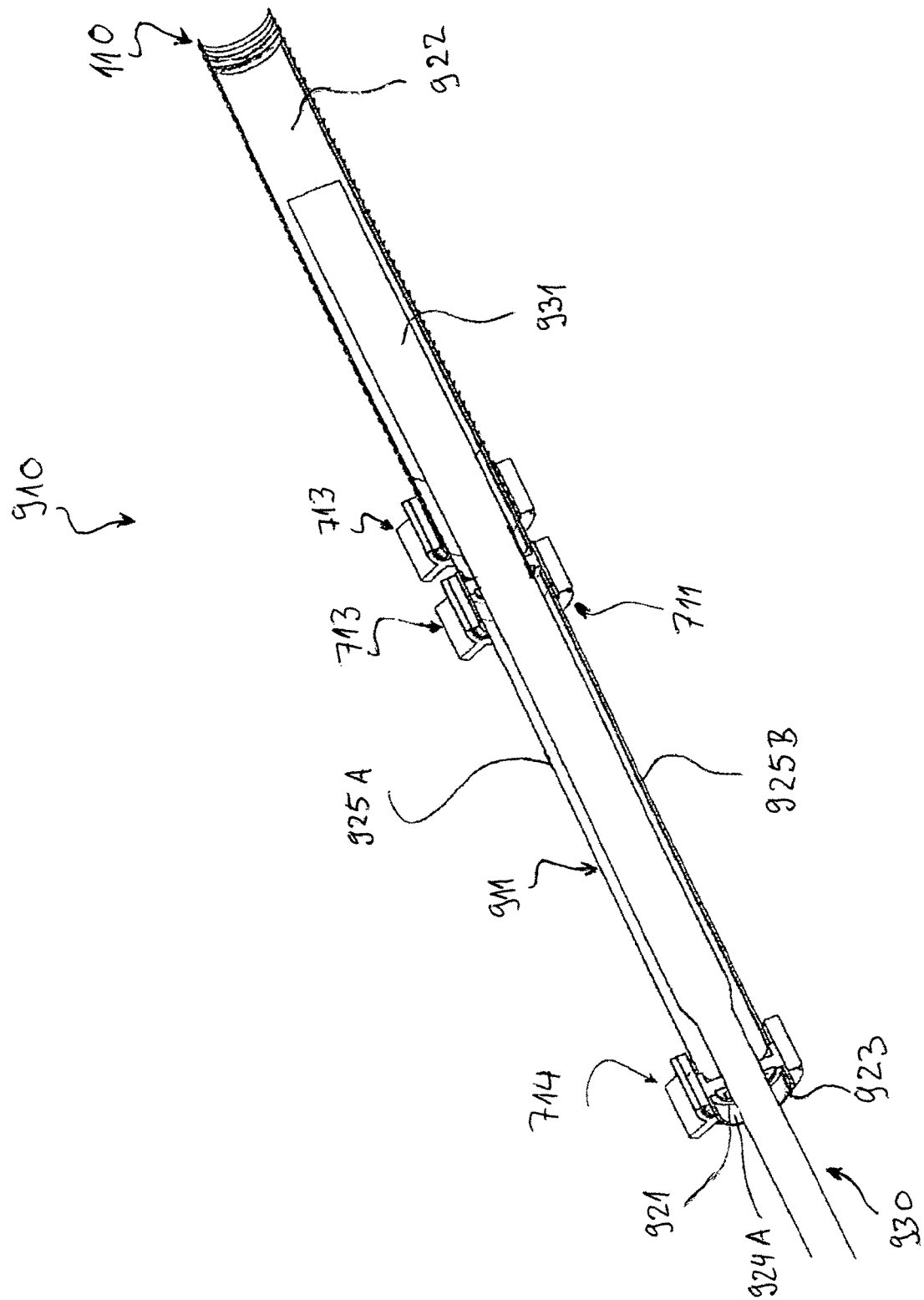
FIG. 17 shows a long introducer sleeve in use with a long device in an assembled cross section view.

Now referring to FIG. 15, FIG. 16 and FIG. 17, another embodiment of a graft system 910 with a long introducer in accordance with the present invention is shown in an exploded view in FIG. 15, a section view in FIG. 16 and an assembled section view in FIG. 17. The graft system 910 with a long introducer comprises a graft 110, a proximal hemostasis valve 711, a distal hemostasis valve 911 with a long introducer sheath, two proximal clamps 713 and a distal clamp 714. The proximal hemostasis valve 711 is similar, to some extent, to the low profile hemostasis valve 610 in feature and function and comprises a proximal hemostasis valve slit membrane 715, a proximal hemostasis valve introducer sheath 716 and a proximal hemostasis valve housing 717. The proximal hemostasis valve housing 717 comprises two distinct halves (whereas one of the halves is shown and indicated as 718A, the other half 718B is not shown in FIG. 16), joined by a proximal hemostasis valve seam 719A and a proximal hemostasis valve seam 719B that travel preferably the entire length of the proximal hemostasis valve 711. The proximal hemostasis valve seams 719A, 719B are intended to thin the wall of the proximal hemostasis valve 711 to provide a preferential breaking line in the event that the proximal hemostasis valve 711 is split in two halves resulting in two separate halves 719A, 719B. A portion or the entire body of the proximal hemostasis valve housing 717 is preferably made of a soft polymer that allows clamping of proximal hemostasis valve slit membrane 715 when clamped with a clamp, such as proximal clamp 713. The proximal hemostasis valve slit membrane 715 is typically a soft rubber disk that comprises proximal hemostasis valve membrane slits 719 and a proximal hemostasis valve center hole 720 to ease the introduction or removal of any solid device through the proximal hemostasis valve 711. A minimum of one slit or a multitude of slits may be included depending on the intended use of the valve. Similarly, the length of the proximal hemostasis valve slits 719 may vary according to the intended use. For example, a hemostasis valve intended to be used in association with a large diameter device would typically have longer proximal hemostasis valve membrane slits 719 as well as a larger diameter proximal hemostasis valve center hole 720.

A barb 740 is provided as a raised surface located on the proximal hemostasis valve introducer sheath 716 to engage the inner surface of the graft 110 and assure a firm grip when the graft 110 is captured between the barb 740 and the proximal clamp 713. The barb 740 may cover a portion or the full circumference of the proximal hemostasis valve introducer sheath 716. The barb 740 may be a single raised surface or multiple raised surfaces radially aligned with or offset from each other to provide greater grip force on the graft 110. The barb 740 may allow a user to tie the graft 110 to the proximal hemostasis valve introducer sheath 716 with sutures, umbilical tape, medical tape or other means. Such a connection between the graft 110 and the proximal hemostasis valve introducer sheath 716 can increase the stability of the access point for insertion and removal of a device.

The distal hemostasis valve 911 with a long introducer sheath is similar to the low profile hemostasis valve 610 in feature and function, except for the distal hemostasis valve 911 having a long introducer sheath sleeve 922. The distal hemostasis valve 911 comprises a distal hemostasis valve slit membrane 921, a distal hemostasis valve sleeve 922 and a distal hemostasis valve housing 923. The distal hemostasis valve housing 923 comprises two distinct halves (whereas one of the halves is shown and indicated as 924A, the other half 924B is not shown in FIGS. 16 and 17), joined by a distal hemostasis valve seam 925A and a distal hemostasis valve seam 925B that travel preferably the entire length of the distal hemostasis valve 911. The distal hemostasis valve seams 925A, 925B are intended to thin the wall of the distal hemostasis valve 911 to provide a preferential breaking line in the event that the distal hemostasis valve 911 is split in two halves resulting in two separate halves 925A, 925B. A portion or the entire body of the distal hemostasis valve housing 923 is preferably made of a soft polymer that allows clamping of the distal hemostasis valve slit membrane 921 when clamped with a clamp, such as distal clamp 714. The distal hemostasis valve slit membrane 921 is typically a soft rubber disk that comprises distal hemostasis valve membrane slits 925 and a distal hemostasis valve center hole 926 (not shown in FIGS. 16 and 17) to ease the introduction or removal of any solid device through the distal hemostasis valve 911 with a long introducer sheath. A minimum of one slit or a multitude of slits may be included depending on the intended use of the valve. Similarly, the length of the distal hemostasis valve sheath slits 925 may vary according to the intended use. For example, a hemostasis valve intended to be used in association with a large diameter device would typically have longer distal hemostasis valve membrane slits 925 as well as a larger diameter distal hemostasis valve center hole 920.

A long device 930 may be a catheter intended for insertion into the human body and comprises an enlarged tip 931 and a thin catheter 932 that is typically smaller in diameter than the enlarged tip 931. The insertion of the long device 930 into the graft 110 without the aid of any hemostasis valve, introducer sheath, or clamps is common practice in the medical field and results in significant blood loss that endangers the patient's safety. The graft system 910 with a long introducer is intended to reduce the risk associated with introducing a medical device through the graft 110. The following is given as an example of a graft system 910 with a long introducer and is not the only way a graft system with a long introducer may be used in the medical field. The distal hemostasis valve sleeve 922 may be of any length, preferably ranging from 1 cm to 200 cm, which will allow the accommodation of the enlarged tip 931 with some excess length left at the proximal and distal ends of the distal hemostasis valve 911. As shown in FIG. 16 and FIG. 17, the long device 930 is positioned inside the distal hemostasis valve 911 with a long introducer sheath, with the thin catheter 932 being positioned through the distal hemostasis valve center hole 926, and the enlarged tip 931 being completely inside the distal hemostasis valve sleeve 922. In some implementations, the graft 110, the proximal clamp 713, and the proximal hemostasis valve sheath 716 are provided in a kit. The kit may include a ruler having length increments and graft angle bevel markings to help a user prepare and cut grafts accurately. A ruler with markings indicating lengths and angles can allow a user to tailor the graft 100 to the patient and situation.

Following graft anastomosis to a vascular vessel or a body cavity per standard medical procedure, the proximal hemostasis valve 711 may be inserted inside the graft 110 and secured in place using the proximal clamp 713. Subsequently, the distal hemostasis valve sleeve 922 may be inserted through the proximal hemostasis valve slit membrane 715 and advanced to a desired depth inside the graft 110 as shown in FIG. 17. Up to this point no blood loss should be encountered. Subsequently, the long device 930 may be advanced further into the graft 110 and into the anastomosed vessel (not shown in FIGS. 15, 16, 17; only shown for reference in FIG. 2) by pushing the thin catheter 932 into the hemostasis valve with long introducer sheath 911. When the enlarged tip 931 reaches its intended position inside the vessel or body cavity, the distal clamp 714 may be clamped to lock the thin catheter 932 in the desired position.

Figure 18:
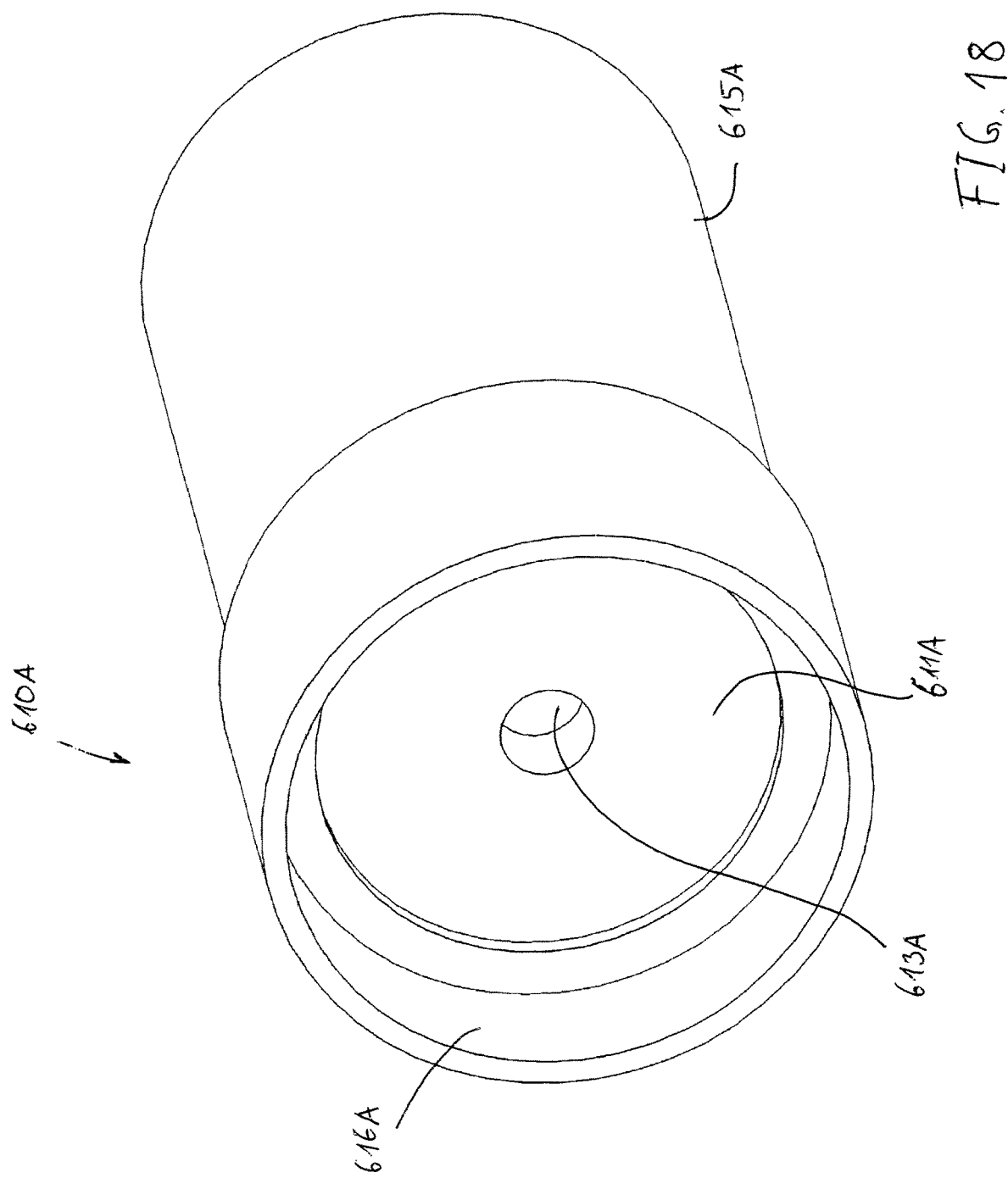
FIG. 18 shows a low profile hemostasis valve having a membrane without slits.
Figure 19:
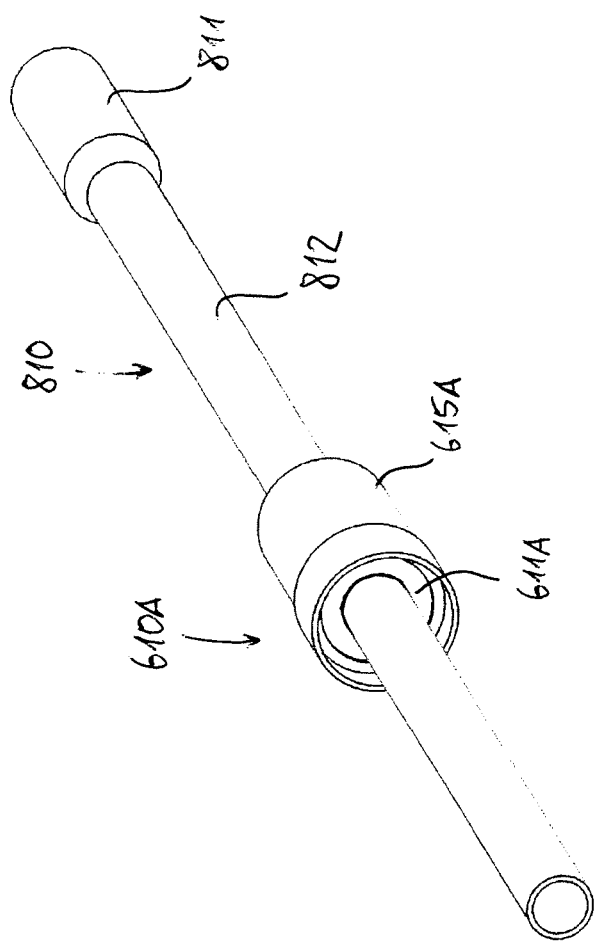
FIG. 19 shows the low profile hemostasis valve pre-mounted on a catheter.

Now referring to FIGS. 18 and 19, another embodiment of a hemostatic valve 610A in accordance with the present invention is shown. The hemostasis valve 610A is similar, to some extent, to the low profile hemostasis valve 610 in feature and function except that the membrane 611A does not have any slits and the hemostatic valve 610A cannot be separated into two halves. The hemostatic valve 610A comprises a hemostasis valve membrane 611A, a hemostasis valve introducer sheath 615A and a hemostasis valve housing 616A. A portion or the entire body of the hemostasis valve housing 616A is preferably made of a soft polymer that allows clamping of the hemostasis valve membrane 611A when clamped with a clamp, such as clamp 210. The hemostasis valve membrane 611A is typically a soft rubber disk and comprises a hemostasis valve center hole 613A to ease the introduction or removal of any solid device through the intermediate hemostasis valve 610A. No slits are included in the membrane 611A, which may improve hemostasis and prevent blood leakage in particular in long term applications. In case a medical device, such as a catheter 810, is pre-mounted in the hemostatic valve 610A (as shown in FIG. 19), no slits are needed in the membrane. The size of the center hole 613A may vary depending on the intended use of the valve. For example, a hemostasis valve intended to be used in association with a large diameter device would typically have a larger diameter hemostasis valve center hole 613A.

Figure 20:
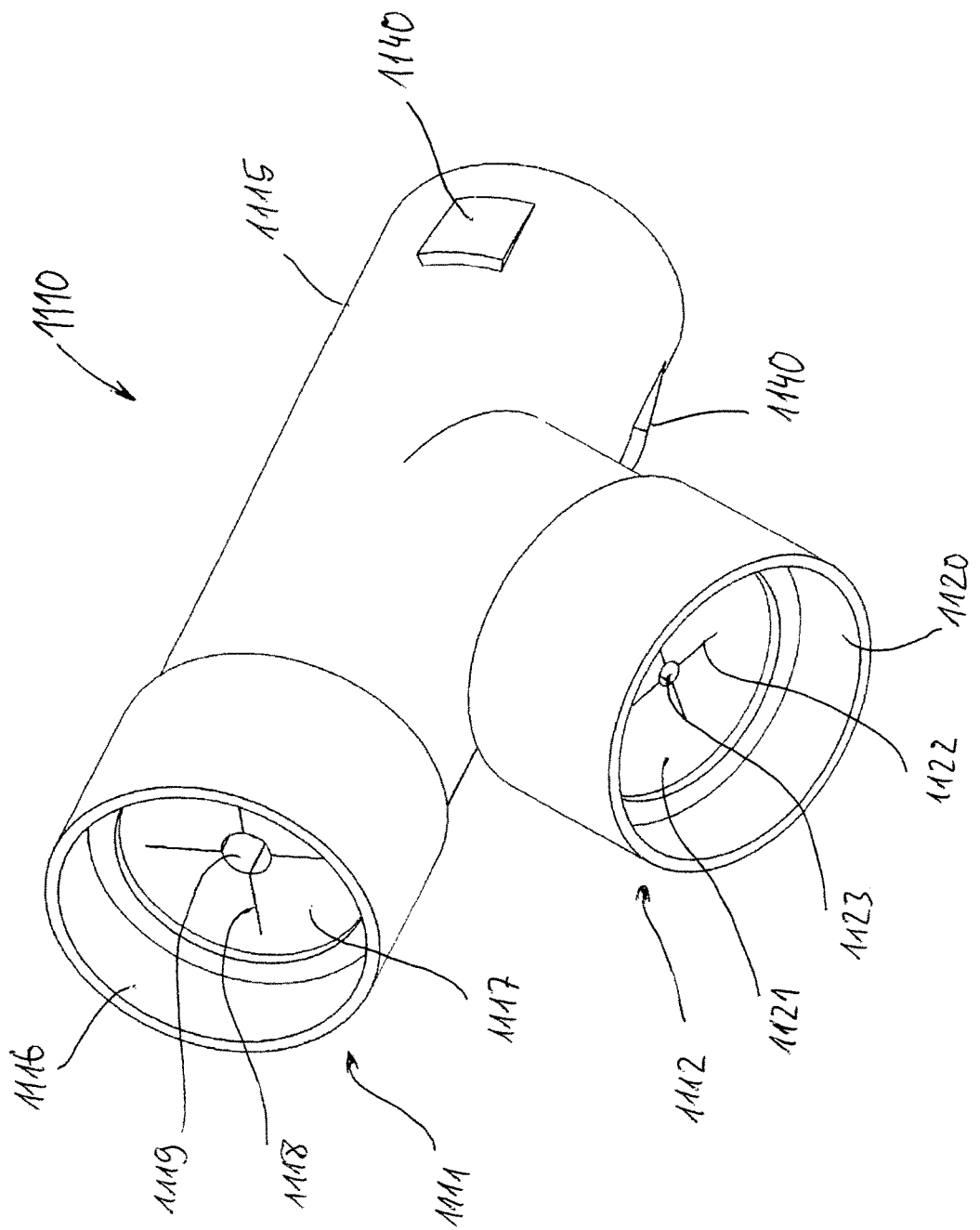
FIG. 20 shows a branched hemostasis valve.

Referring to FIG. 20, an embodiment of a branched hemostasis valve 1110 in accordance with the present invention is shown. The hemostasis valve 1110 is similar, to some extent, to the low profile hemostasis valve 610 in feature and function. However, in contrast to a stack of multiple hemostatic valves arranged in series, as shown in FIGS. 9 to 17, the branched hemostatic valve 1110 comprises two hemostatic valves 1111, 1112 that are arranged parallel in a branched or Y configuration. With regard to the features and functions reference is made to the above description, in particular with regard to the low profile hemostatic valve. The hemostatic valve 1111 comprises a housing 1116 with a slit membrane 1117. The membrane 1117 has slits 1118 and a central hole 1119. Accordingly, the hemostatic valve 1112 comprises a housing 1120 with a slit membrane 1121. The membrane 1121 has slits 1122 and a central hole 1123. The branched hemostatic valve 1110 comprises an introducer sheath 1115 having barbs 1140 that function as described above in connection with barbs 740. The branched hemostatic valve 1110 allows parallel and independent insertion and manipulation of two medical devices, such as a catheter and a guide wire. For this purpose the central holes 1119 and 1123 are different in size to provide a tight connection to the respective medical device. In particular, as described in connection with the aforementioned embodiments, the housings 1116 and 1120 may have a portion made of a soft material to allow clamping of the membranes 1117 and 1121, respectively, for example by means of a clamp 210.

It will be appreciated that various features of the described hemostatic valves and clamps may be combined and are not limited to the disclosed combinations. In particular, any of the disclosed hemostatic valves may have a retention structure, such as one or more barbs, on the outer surface of the introducer sheath. Further, any of the disclosed hemostatic valves may have seams so as to be separable into two halves or may be made of one piece without seams.

Figure 21:
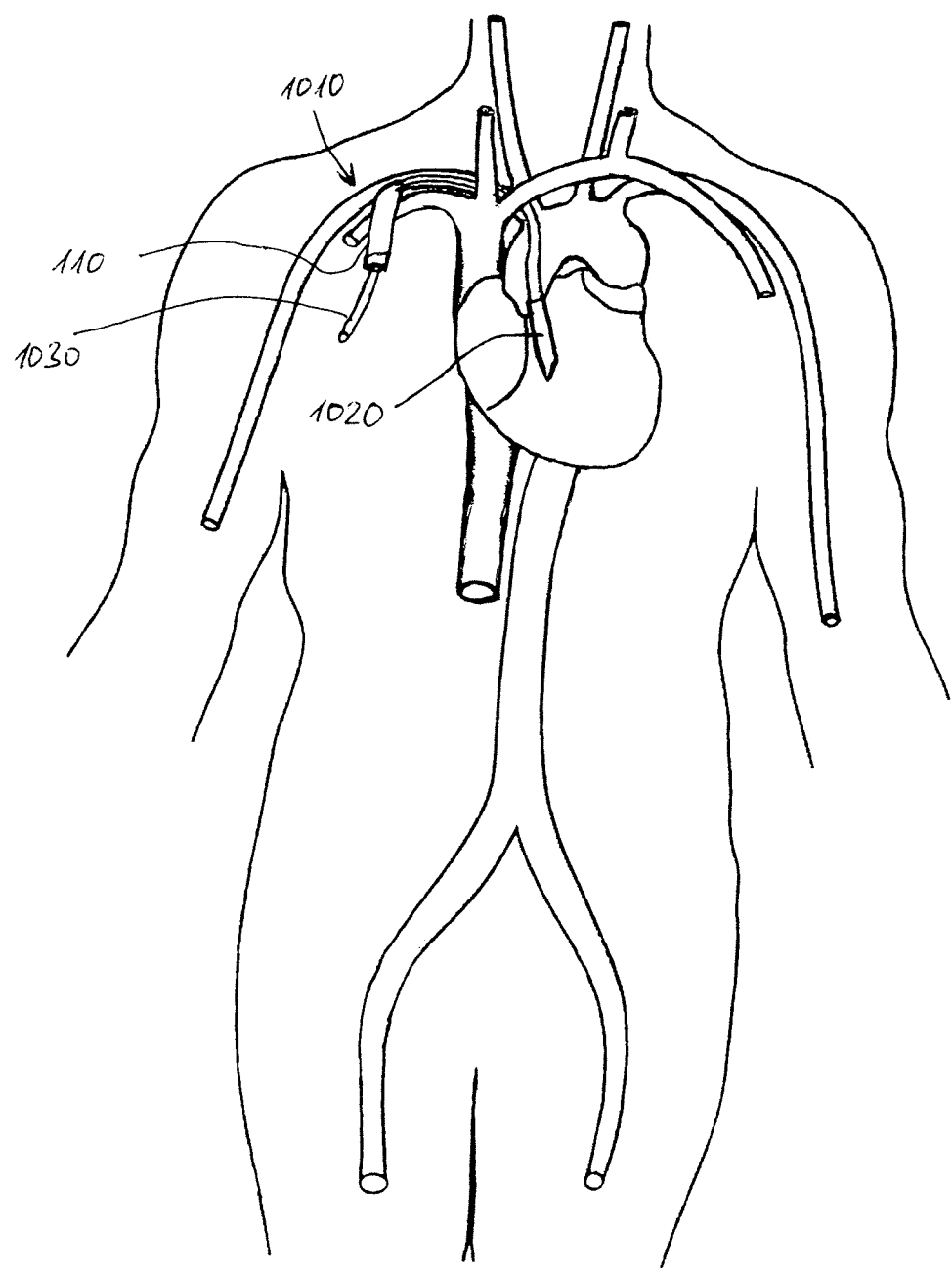
FIG. 21 shows an application of the system of the invention.
Figure 22:
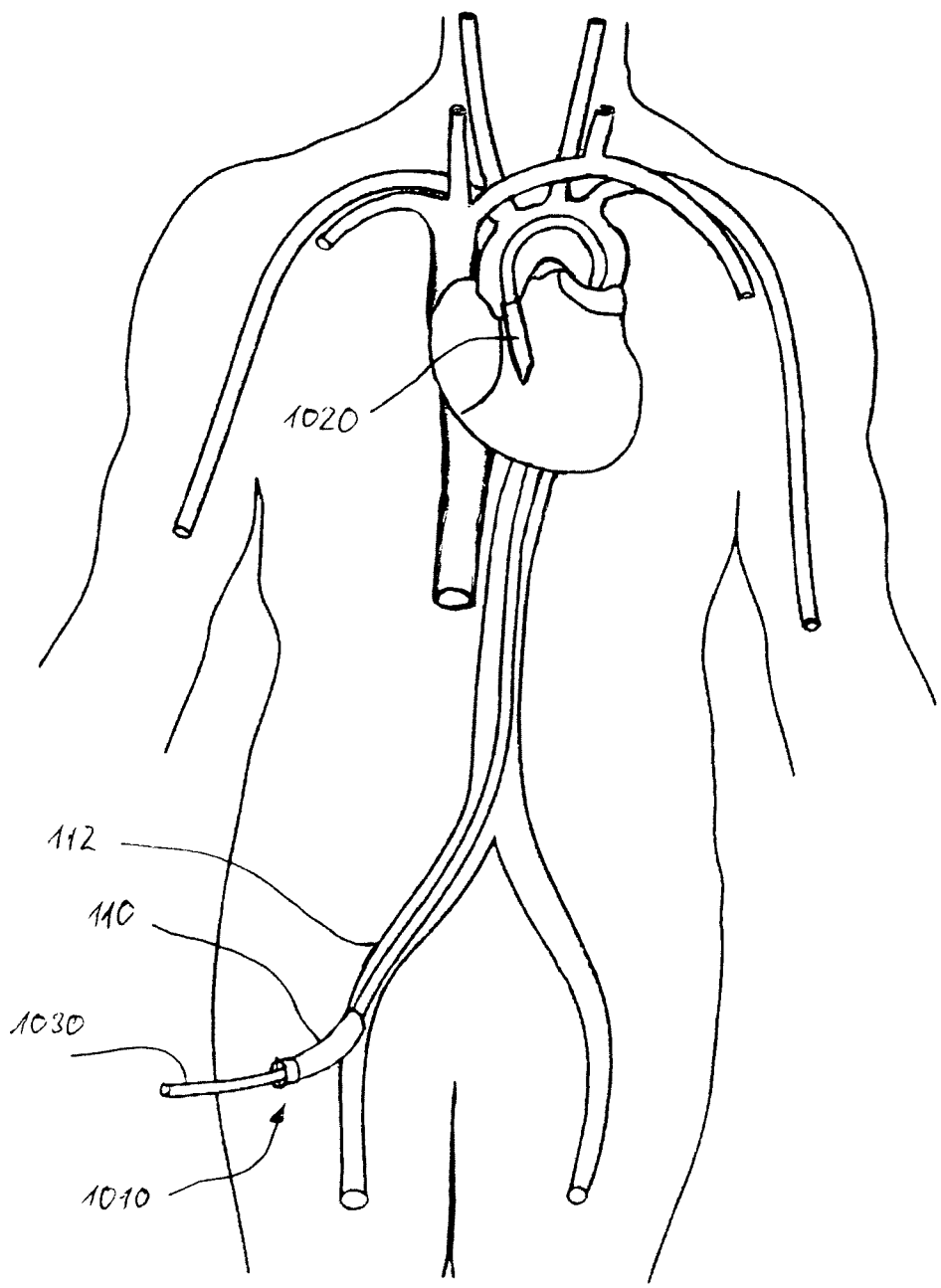
FIG. 22 shows another application of the system of the invention.

Referring now to FIGS. 21 and 22, applications of a graft system 1010 are shown. The graft system 1010 may be in accordance with any one of the above disclosed systems. It is used to deliver an axial blood pump 1020 by means of a catheter 1030 through a patient's aorta into the patient's heart to provide a ventricular assistant device. The vascular access may be placed in a peripheral vessel in the patient's thorax (FIG. 21) or in the patient's groin (FIG. 22). Referring to FIG. 21, the graft system 1010 may be completely implanted subcutaneously when using one or more low profile hemostatic valves as described above.

The invention claimed is:

1. A system for providing vascular access in a patient's body, comprising:
   a vascular graft comprising a tubular body having a proximal end and a distal end, the proximal end being configured to be attached to a vessel in a patient's body;
   at least two valves, comprising at least:
      a first valve configured to be attached to the distal end of the vascular graft's tubular body, the first valve comprising a housing, the housing including a flexible membrane configured to maintain hemostasis when the proximal end of the vascular graft is attached to a vessel in a patient's body and a medical device is inserted through the membrane into said vascular graft, the first valve further comprising a first projecting portion configured to be inserted into the distal end of the vascular graft's tubular body; and
      a second valve comprising a second projecting portion configured to be connectable to a distal end of the first valve so that the first valve and the second valve may be attached in series at the distal end of the vascular graft, the second projecting portion having a length that is at least ten times an outer diameter of the second projecting portion; and
   at least one clamp comprising an annular ring with first and second ends, the at least one clamp being configured to be disposed around the vascular graft's tubular body and having a first configuration that allows insertion of the first projecting portion into the distal end of the vascular graft's tubular body, and a second configuration that allows clamping of the vascular graft against the first projecting portion when the first projecting portion is inserted in the vascular graft's tubular body, the second configuration being one in which the first end of the annular ring overlaps the second end of the annular ring.

2. The system of claim 1, wherein an outer surface of the first projecting portion includes at least one retention structure so as to prevent removal of the first valve from the vascular graft.

3. The system of claim 2, wherein the retention structure is formed as a ramped surface.

4. The system of claim 3, wherein the retention structure comprises at least one barb that tapers away from the outer surface of the first projecting portion in a direction towards the housing.

5. The system of claim 1, wherein, in addition to the membrane, at least a portion of the housing is made of a flexible material.

6. The system of claim 5, wherein the first projecting portion is stiffer with respect to radial compression forces than a portion of the housing where the membrane is located.

7. The system of claim 5, wherein the flexible material is an elastic material.

8. The system of claim 1, wherein the housing is cylindrical.

9. The system of claim 1, wherein an inner diameter of the first projecting portion does not decrease at a proximal end of the first projecting portion.

10. The system of claim 1, wherein the flexible membrane has at least one passage that extends along a portion of a diameter of the membrane, or along an entire diameter of the membrane.

11. The system of claim 1, wherein the membrane has a hole extending through the membrane.

12. The system of claim 1, wherein the first valve includes at least one seam extending along a length of the first valve and forming a predetermined breaking line to allow breaking of the first valve.

13. The system of claim 1, wherein the housing has at least one handle extending radially outwards from the housing.

14. The system of claim 1, wherein the second projecting portion is configured to be inserted into the housing of the first valves.

15. The system of claim 1, wherein the first valve and the second valve both haves a membrane with a central hole, and wherein a diameter of the central hole in the membrane of the first valve is larger than a diameter of the central hole in the membrane of the second valve.

16. The system of claim 1, wherein the medical device is a catheter.

17. The system of claim 16, wherein the medical device comprises an axial blood pump arranged at a tip of the catheter.

18. The system of claim 1, wherein an inner diameter of the first projecting portion is constant along an entire length of the first projecting portion.

19. The system of claim 1, wherein the flexible membrane has at least one passage in the membrane, the at least one passage comprising at least two slits extending diametrically through the membrane and crossing each other.

20. The system of claim 1, wherein the first valve includes two diametrically opposing seams, each seam extending along a length of the first valve and forming a predetermined breaking line to allow breaking of the first valve into two halves along the length of the first valve.

21. The system of claim 1, wherein the housing has two diametrically opposed handles, each handle extending radially outwards from the housing.

22. A system for providing vascular access in a patient's body, comprising:

a vascular graft comprising a tubular body having a proximal end and a distal end, the proximal end being configured to be attached to a vessel in a patient's body;

at least two valves, comprising at least:

a first valve configured to be attached to the distal end of the vascular graft's tubular body, the first valve comprising a housing, the housing including a flexible membrane configured to maintain hemostasis when the proximal end of the vascular graft is attached to a vessel in a patient's body and a medical device is inserted through the membrane into said vascular graft, the first valve further comprising a first projecting portion configured to be inserted into the distal end of the vascular graft's tubular body; and a second valve comprising a second projecting portion configured to be connectable to a distal end of the first valve so that the first valve and the second valve may be attached in series at the distal end of the vascular graft;

at least one clamp comprising an annular ring with first and second ends, the at least one clamp being configured to be disposed around the vascular graft's tubular body and having a first configuration that allows insertion of the first projecting portion into the distal end of the vascular graft's tubular body, and a second configuration that allows clamping of the vascular graft against the first projecting portion when the first projecting portion is inserted in the vascular graft's tubular body, the second configuration being one in which the first end of the annular ring overlaps the second end of the annular ring; and at least one secondary clamp configured to be disposed around the housing of the first valve.

23. The system of claim 22, wherein the at least one secondary clamp is configured to be joined together with the at least one clamp.

* * * * *

UNITED STATES PATENT AND TRADEMARK OFFICE
CERTIFICATE OF CORRECTION

PATENT NO. : 11,179,556 B2  
APPLICATION NO. : 15/517937  
DATED : November 23, 2021  
INVENTOR(S) : Glen Fantuzzi et al.

Page 1 of 1

It is certified that error appears in the above-identified patent and that said Letters Patent is hereby corrected as shown below:

In the Specification

Column 8, Line 66, Delete "212." and insert --211.-- therefor  
Column 11, Line 9, Delete "710." and insert --713.-- therefor  
Column 11, Line 34, Delete "711" and insert --712-- therefor  
Column 11, Line 39, Delete "713." and insert --714.-- therefor  
Column 11, Line 44, Delete "711." and insert --712.-- therefor  
Column 14, Line 48, Delete "100" and insert --110-- therefor In the Claims Column 17, Claim 15, Line 18, delete "haves" and insert --have-- therefor Signed and Sealed this  
Fifteenth Day of March, 2022

Drew Hirshfeld  
*Performing the Functions and Duties of the*  
*Under Secretary of Commerce for Intellectual Property and*  
*Director of the United States Patent and Trademark Office*